US012693255B2

(12) United States Patent
Ouyang et al.

(10) Patent No.: US 12,693,255 B2
(45) Date of Patent: Jul. 28, 2026

(54) ANALYTE SENSORS AND SENSING METHODS FOR DETECTING CREATININE

(71) Applicant: Abbott Diabetes Care Inc., Alameda, CA (US)

(72) Inventors: Tianmei Ouyang, Fremont, CA (US); Benjamin J. Feldman, Berkeley, CA (US); Hyun Cho, Berkeley, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 566 days.

(21) Appl. No.: 16/582,583

(22) Filed: Sep. 25, 2019

(65) Prior Publication Data

US 2020/0241015 A1 Jul. 30, 2020

Related U.S. Application Data

(60) Provisional application No. 62/884,869, filed on Aug. 9, 2019, provisional application No. 62/884,841, filed (Continued)

(51) Int. Cl.

*G01N 33/70* (2006.01)
*A61B 5/145* (2006.01)

(Continued)

(52) U.S. Cl.

CPC ....... *G01N 27/3271* (2013.01); *A61B 5/1451* (2013.01); *A61B 5/14532* (2013.01);

(Continued)

(58) Field of Classification Search

CPC .............. A61B 5/1451; A61B 5/14532; A61B 5/14546; A61B 5/1486–14865;

(Continued)

(56) References Cited

U.S. PATENT DOCUMENTS

| | | | |
|---|---|---|---|
| 4,321,123 | A | 3/1982 | Nakamura et al. |
| 4,721,677 | A | 1/1988 | Clark, Jr. |

(Continued)

FOREIGN PATENT DOCUMENTS

| | | | |
|---|---|---|---|
| CN | 1735375 | A | 2/2006 |
| CN | 101849180 | B | 8/2017 |

(Continued)

OTHER PUBLICATIONS

T. Monteiro, P.R. Rodrigues, A. L. Gonçalves, J.J.G. Moura, E. Jubete, L. Añorga, B. Piknova, A.N. Schechter, C.M. Silveira, M. G. Almeida, "Construction of effective disposable biosensors for point of care testing of nitrite," Sep. 1, 2015, Talanta,vol. 142, pp. 246-251 (Year: 2015).*

(Continued)

*Primary Examiner* — Brian L Casler
(74) *Attorney, Agent, or Firm* — Sterne, Kessler, Goldstein & Fox P.L.L.C.

(57) ABSTRACT

Creatinine levels may be monitored as a measure of kidney function. Conventionally, blood and/or urine tests are used for this purpose. Analyte sensors capable of monitoring creatinine in vivo may comprise: a sensor tail comprising at least a first working electrode, a creatinine-responsive active area disposed upon a surface of the first working electrode, a first membrane that is permeable to creatinine and over-coats the creatinine-responsive active area, and an oxygen scavenger located upon the sensor tail in proximity to the creatinine-responsive active area. The creatinine-responsive active area comprises a first electron transfer agent, a first polymer, and an enzyme system comprising multiple enzymes, particularly creatinine amidohydrolase, creatine amidinohydrolase, and sarcosine oxidase, that are capable of acting in concert to facilitate detection of creatinine. An oxidase enzyme may serve as the oxygen scavenger, par- (Continued)

ticularly glucose oxidase when detecting creatinine in fluids also containing glucose.

16 Claims, 10 Drawing Sheets

Related U.S. Application Data on Aug. 9, 2019, provisional application No. 62/797,566, filed on Jan. 28, 2019.

(51) Int. Cl.

| | |
|---|---|
| ***A61B 5/1473*** | (2006.01) |
| ***A61B 5/1486*** | (2006.01) |
| ***C12Q 1/00*** | (2006.01) |
| ***G01N 27/327*** | (2006.01) |

(52) U.S. Cl.

CPC ...... *A61B 5/14546* (2013.01); *A61B 5/14735* (2013.01); *A61B 5/1486* (2013.01); *A61B 5/14865* (2013.01); *C12Q 1/002* (2013.01); *C12Q 1/005* (2013.01); *C12Q 1/006* (2013.01); *G01N 27/327* (2013.01); *A61B 2562/02* (2013.01); *C12Y 101/03004* (2013.01); *C12Y 105/03001* (2013.01); *C12Y 305/0201* (2013.01); *C12Y 305/03003* (2013.01); *G01N 2333/904* (2013.01); *G01N 2333/90683* (2013.01); *G01N 2333/978* (2013.01); *G01N 2333/986* (2013.01)

(58) Field of Classification Search

CPC ............ A61B 5/14735; A61B 2562/02; A61B 5/14503; A61B 5/1473; G01N 27/3271–3272; G01N 33/49; G01N 33/493; G01N 33/5306; G01N 33/70; G01N 2333/90683; G01N 2333/986; G01N 2333/978; G01N 27/327; G01N 2333/904; C12Y 305/0201; C12Y 305/03003; C12Y 101/03004; C12Y 105/03001; C12Q 1/001–006; C12Q 1/26; C12Q 1/34

USPC .......................................................... 600/345

See application file for complete search history.

(56) References Cited

U.S. PATENT DOCUMENTS

| | | | |
|---|---|---|---|
| 5,262,035 | A | 11/1993 | Gregg et al. |
| 5,264,105 | A | 11/1993 | Gregg et al. |
| 5,322,063 | A | 6/1994 | Allen et al. |
| 5,356,786 | A | 10/1994 | Heller et al. |
| 5,593,852 | A | 1/1997 | Heller et al. |
| 5,696,314 | A | 12/1997 | McCaffrey et al. |
| 5,783,056 | A | 7/1998 | Hampp et al. |
| 5,792,621 | A | 8/1998 | Verostko et al. |
| 5,793,621 | A | 8/1998 | Yamada |
| 5,820,551 | A | 10/1998 | Hill et al. |
| 5,965,105 | A | 10/1999 | Rayalu et al. |
| 5,965,106 | A | 10/1999 | Pomato et al. |
| 6,071,391 | A | 6/2000 | Gotoh et al. |
| 6,121,009 | A | 9/2000 | Heller et al. |
| 6,134,461 | A | 10/2000 | Say et al. |
| 6,175,752 | B1 | 1/2001 | Say et al. |
| 6,241,863 | B1 | 6/2001 | Monbouquette |
| 6,284,478 | B1 | 9/2001 | Heller et al. |
| 6,377,894 | B1 | 4/2002 | Deweese et al. |
| 6,503,381 | B1 | 1/2003 | Gotoh et al. |
| 6,514,460 | B1 | 2/2003 | Fendrock |
| 6,514,718 | B2 | 2/2003 | Heller et al. |
| 6,541,216 | B1 | 4/2003 | Wilsey et al. |
| 6,560,471 | B1 | 5/2003 | Heller et al. |
| 6,579,690 | B1 | 6/2003 | Bonnecaze et al. |
| 6,600,997 | B2 | 7/2003 | Deweese et al. |
| 6,605,200 | B1 | 8/2003 | Mao et al. |
| 6,605,201 | B1 | 8/2003 | Mao et al. |
| 6,654,625 | B1 | 11/2003 | Say et al. |
| 6,676,816 | B2 | 1/2004 | Mao et al. |
| 6,736,957 | B1 | 5/2004 | Forrow |
| 6,746,582 | B2 | 6/2004 | Heller et al. |
| 6,881,551 | B2 | 4/2005 | Heller et al. |
| 6,932,894 | B2 | 8/2005 | Mao et al. |
| 6,946,299 | B2 | 9/2005 | Neel et al. |
| 7,090,756 | B2 | 8/2006 | Mao et al. |
| 7,299,082 | B2 | 11/2007 | Feldman et al. |
| 7,501,053 | B2 | 3/2009 | Karinka et al. |
| 7,520,970 | B2 | 4/2009 | Sato et al. |
| 7,563,588 | B2 | 7/2009 | Gao et al. |
| 7,754,093 | B2 | 7/2010 | Forrow et al. |
| 7,811,231 | B2 | 10/2010 | Jin et al. |
| 7,822,557 | B2 | 10/2010 | Chen et al. |
| 8,106,780 | B2 | 1/2012 | Goodnow |
| 8,268,143 | B2 | 9/2012 | Liu et al. |
| 8,435,682 | B2 | 5/2013 | Heller |
| 8,444,834 | B2 | 5/2013 | Liu et al. |
| 8,545,693 | B2 | 10/2013 | Mccoll et al. |
| 8,761,857 | B2 | 6/2014 | Feldman et al. |
| 8,911,908 | B2 | 12/2014 | Sakai et al. |
| 9,290,839 | B2 | 3/2016 | Wang et al. |
| 9,775,549 | B2 | 10/2017 | Ouyang et al. |
| 9,914,952 | B2 | 3/2018 | Ouyang et al. |
| 9,927,386 | B2 | 3/2018 | Wang et al. |
| 9,983,161 | B2 | 5/2018 | Feldman et al. |
| 10,022,076 | B2 | 7/2018 | Hoss et al. |
| 10,136,816 | B2 | 11/2018 | Bernstein et al. |
| 10,201,301 | B2 | 2/2019 | Heller et al. |
| 10,702,193 | B2 | 7/2020 | Simpson et al. |
| 11,091,788 | B2 | 8/2021 | Ouyang et al. |
| 2001/0003045 | A1 | 6/2001 | Davis et al. |
| 2003/0042137 | A1 | 3/2003 | Mao et al. |
| 2003/0050547 | A1 | 3/2003 | Lebel et al. |
| 2003/0068666 | A1 | 4/2003 | Zweig |
| 2003/0100821 | A1 | 5/2003 | Heller et al. |
| 2004/0061232 | A1 | 4/2004 | Shah et al. |
| 2005/0148832 | A1 | 7/2005 | Reghabi et al. |
| 2005/0215871 | A1 | 9/2005 | Feldman et al. |
| 2006/0004272 | A1 | 1/2006 | Shah |
| 2006/0076236 | A1 | 4/2006 | Shah et al. |
| 2006/0257996 | A1 | 11/2006 | Simpson et al. |
| 2007/0007132 | A1 | 1/2007 | Mao et al. |
| 2007/0027385 | A1 | 2/2007 | Brister et al. |
| 2007/0042377 | A1 | 2/2007 | Gao et al. |
| 2007/0095661 | A1 | 5/2007 | Wang et al. |
| 2007/0131547 | A1 | 6/2007 | Nomoto et al. |
| 2007/0213611 | A1 | 9/2007 | Simpson et al. |
| 2007/0235331 | A1 | 10/2007 | Simpson et al. |
| 2007/0270672 | A1 | 11/2007 | Hayter |
| 2008/0179187 | A1 | 7/2008 | Ouyang et al. |
| 2008/0319295 | A1 | 12/2008 | Bernstein et al. |
| 2009/0166194 | A1 | 7/2009 | Sato et al. |
| 2009/0294306 | A1* | 12/2009 | Feldman .............. G01N 27/301 205/792 |
| 2010/0185070 | A1 | 7/2010 | Brister et al. |
| 2010/0198034 | A1 | 8/2010 | Thomas et al. |
| 2010/0213057 | A1 | 8/2010 | Feldman et al. |
| 2010/0230285 | A1 | 9/2010 | Hoss et al. |
| 2010/0267161 | A1 | 10/2010 | Wu et al. |
| 2010/0268043 | A1 | 10/2010 | Yodfat et al. |
| 2010/0324392 | A1 | 12/2010 | Yee et al. |
| 2010/0326842 | A1 | 12/2010 | Mazza et al. |
| 2011/0039165 | A1 | 2/2011 | Sugiyama et al. |
| 2011/0046467 | A1 | 2/2011 | Simpson et al. |
| 2011/0065008 | A1 | 3/2011 | Nakagawa et al. |
| 2011/0120865 | A1 | 5/2011 | Bommakanti et al. |
| 2011/0124993 | A1 | 5/2011 | Bommakanti et al. |
| 2011/0124994 | A1 | 5/2011 | Bommakanti et al. |
| 2011/0126188 | A1 | 5/2011 | Bernstein et al. |
| 2011/0213057 | A1 | 9/2011 | Fenn et al. |
| 2011/0213225 | A1 | 9/2011 | Bernstein et al. |
| 2011/0256024 | A1 | 10/2011 | Cole et al. |

(56) References Cited

U.S. PATENT DOCUMENTS

| | | | |
|---|---|---|---|
| 2011/0257495 A1 | 10/2011 | Hoss et al. | |
| 2012/0132525 A1 | 5/2012 | Liu et al. | |
| 2012/0138484 A1 | 6/2012 | Bommakanti et al. | |
| 2012/0150005 A1* | 6/2012 | Hoss | A61B 5/14532 600/347 |
| 2012/0157801 A1 | 6/2012 | Hoss et al. | |
| 2012/0181189 A1 | 7/2012 | Merchant | |
| 2012/0186997 A1 | 7/2012 | Li et al. | |
| 2012/0245447 A1 | 9/2012 | Karan et al. | |
| 2012/0283537 A1 | 11/2012 | Petisce et al. | |
| 2012/0296186 A1 | 11/2012 | Ouyang et al. | |
| 2012/0323098 A1 | 12/2012 | Moein et al. | |
| 2013/0059212 A1 | 3/2013 | Kusumegi et al. | |
| 2013/0116524 A1 | 5/2013 | Cole et al. | |
| 2013/0131478 A1 | 5/2013 | Simpson et al. | |
| 2013/0211219 A1 | 8/2013 | Coppeta et al. | |
| 2013/0231542 A1 | 9/2013 | Simpson et al. | |
| 2013/0245412 A1 | 9/2013 | Rong et al. | |
| 2013/0324820 A1 | 12/2013 | Petillo et al. | |
| 2014/0054171 A1 | 2/2014 | Feldman et al. | |
| 2014/0127728 A1 | 5/2014 | Wilsey | |
| 2014/0176338 A1 | 6/2014 | He et al. | |
| 2014/0262776 A1* | 9/2014 | Martin | G01N 27/3271 204/403.14 |
| 2014/0262777 A1* | 9/2014 | Zhao | C23C 14/58 427/2.13 |
| 2015/0038814 A1 | 2/2015 | Staib et al. | |
| 2015/0076004 A1 | 3/2015 | Gerber et al. | |
| 2015/0207796 A1 | 7/2015 | Love et al. | |
| 2016/0045147 A1 | 2/2016 | Ouyang et al. | |
| 2016/0319232 A1 | 11/2016 | Noritomi et al. | |
| 2016/0328991 A1 | 11/2016 | Simpson et al. | |
| 2016/0345882 A1 | 12/2016 | Wu et al. | |
| 2016/0354542 A1 | 12/2016 | Ward et al. | |
| 2016/0355862 A1 | 12/2016 | Deng et al. | |
| 2017/0156652 A1 | 6/2017 | Qiang | |
| 2017/0191958 A1 | 7/2017 | Gerber et al. | |
| 2017/0202491 A1 | 7/2017 | Heller et al. | |
| 2017/0315077 A1 | 11/2017 | Rao et al. | |
| 2017/0319111 A1 | 11/2017 | Simpson et al. | |
| 2018/0014766 A1 | 1/2018 | Ouyang et al. | |
| 2018/0116604 A1 | 5/2018 | Newberry | |
| 2018/0275088 A1 | 9/2018 | Huff et al. | |
| 2019/0004005 A1 | 1/2019 | Oja et al. | |
| 2019/0024130 A1 | 1/2019 | Ouyang et al. | |
| 2019/0125230 A1 | 5/2019 | Feldman | |
| 2019/0271658 A1 | 9/2019 | Haneda et al. | |
| 2019/0274598 A1* | 9/2019 | Scott | A61B 5/14546 |
| 2019/0320947 A1 | 10/2019 | Chen et al. | |
| 2020/0069226 A1* | 3/2020 | Hahn | A61B 5/14546 |
| 2020/0237275 A1 | 7/2020 | Feldman et al. | |
| 2020/0237276 A1 | 7/2020 | Oja et al. | |
| 2020/0237277 A1 | 7/2020 | Ouyang et al. | |
| 2021/0137431 A1 | 5/2021 | Oja et al. | |
| 2022/0056500 A1 | 2/2022 | Ouyang et al. | |
| 2022/0168727 A1* | 6/2022 | Baldwa | B01L 3/502738 |
| 2022/0386910 A1 | 12/2022 | Oja et al. | |
| 2022/0389475 A1 | 12/2022 | Ouyang et al. | |
| 2022/0395202 A1 | 12/2022 | Ouyang et al. | |
| 2022/0396820 A1 | 12/2022 | Ouyang et al. | |
| 2023/0054564 A1 | 2/2023 | Ouyang et al. | |
| 2023/0080107 A1 | 3/2023 | Ouyang et al. | |
| 2023/0118818 A1 | 4/2023 | Feldman et al. | |
| 2023/0119512 A1 | 4/2023 | Feldman et al. | |
| 2023/0121101 A1 | 4/2023 | Feldman et al. | |
| 2023/0121367 A1 | 4/2023 | Feldman et al. | |
| 2023/0121769 A1 | 4/2023 | Feldman et al. | |
| 2023/0122702 A1 | 4/2023 | Feldman et al. | |
| 2023/0123384 A1 | 4/2023 | Feldman et al. | |
| 2023/0128038 A1 | 4/2023 | Feldman et al. | |
| 2024/0247297 A1 | 7/2024 | Ouyang et al. | |
| 2024/0350047 A1 | 10/2024 | Oja et al. | |
| 2025/0221643 A1 | 7/2025 | Ouyang et al. | |
| 2025/0261884 A1 | 8/2025 | Oja et al. | |
| 2026/0002188 A1 | 1/2026 | Ouyang et al. | |
| 2026/0002189 A1 | 1/2026 | Ouyang et al. | |
| 2026/0002190 A1 | 1/2026 | Ouyang et al. | |
| 2026/0002191 A1 | 1/2026 | Ouyang et al. | |
| 2026/0002192 A1 | 1/2026 | Ouyang et al. | |
| 2026/0002193 A1 | 1/2026 | Ouyang et al. | |
| 2026/0020797 A1 | 1/2026 | Oja et al. | |
| 2026/0020798 A1 | 1/2026 | Oja et al. | |
| 2026/0020799 A1 | 1/2026 | Oja et al. | |

FOREIGN PATENT DOCUMENTS

| | | | |
|---|---|---|---|
| CN | 113164106 | A | 7/2021 |
| EP | 000409435 | A1 | 1/1991 |
| EP | 0990706 | A1 | 4/2000 |
| EP | 3394252 | A1 | 10/2018 |
| EP | 3414325 | A1 | 12/2018 |
| EP | 3597765 | A1 | 1/2020 |
| EP | 4084689 | A1 | 11/2022 |
| GB | 2067764 | A | 7/1981 |
| JP | 03-053896 | A | 3/1991 |
| JP | 2001506742 | A | 5/2001 |
| JP | 2007510155 | A | 4/2007 |
| JP | 2007290504 | A | 11/2007 |
| JP | 2008516235 | A | 5/2008 |
| JP | 2010517054 | A | 5/2010 |
| JP | 2010530790 | A | 9/2010 |
| JP | 2011136186 | A | 7/2011 |
| JP | 2013504053 | A | 2/2013 |
| JP | 2014503080 | A | 2/2014 |
| JP | 2014160024 | A | 9/2014 |
| JP | 2015198960 | A | 11/2015 |
| JP | 2018029983 | A | 3/2018 |
| JP | 2019039817 | A | 3/2019 |
| JP | 2022172249 | A | 11/2022 |
| WO | WO-03056319 | A2 | 7/2003 |
| WO | WO-2005040404 | A1 | 5/2005 |
| WO | WO-2006042001 | A2 | 4/2006 |
| WO | WO-2008041984 | A1 | 4/2008 |
| WO | WO-2009105337 | A2 | 8/2009 |
| WO | WO-2010030912 | A1 | 3/2010 |
| WO | WO-2011030093 | A1 | 3/2011 |
| WO | WO-2012100130 | A1 | 7/2012 |
| WO | WO-2015150263 | A1 | 10/2015 |
| WO | WO-2015195352 | A1 | 12/2015 |
| WO | WO-2016025064 | A1 | 2/2016 |
| WO | WO-2016174456 | A1 | 11/2016 |
| WO | WO-2016174458 | A1 | 11/2016 |
| WO | WO-2017151952 | A1 | 9/2017 |
| WO | WO-2018067235 | A1 | 4/2018 |
| WO | WO-2018106129 | A1 | 6/2018 |
| WO | WO-2019006413 | A1 | 1/2019 |

OTHER PUBLICATIONS

Guiseppi-Elie et al, "Design of a Subcutaneous Implantable Biochip for Monitoring of Glucose and Lactate," IEEE Sensors Journal, Jun. 1, 2005.

C.S. Pundir et al, "Biosensing Methods for Determination of Creatinine: A Review," Biosensors and Bioelectronics Journal, Nov. 19, 2018.

ISRWO in corresponding PCT/US2019/052942 with mail date Nov. 28, 2019.

Cardosi, M., et al., "Amperometric Glucose Sensors for Whole Blood Measurement Based on Dehydrogenase Enzymes," in Dehydrogenases, InTech, United Kingdom (Nov. 2012).

Office Action mailed Apr. 18, 2022 in U.S. Appl. No. 16/774,835, Feldman, B., et al., filed Jan. 28, 2020, 24 pages.

Office Action mailed Jun. 2, 2022 in U.S. Appl. No. 16/774,909, Ouyang, T., et al., filed Jan. 28, 2020, 13 pages.

Office Action mailed Jun. 24, 2022 in U.S. Appl. No. 16/774,841, Oja, S., et al., filed Jan. 28, 2020, 10 pages.

Office Action mailed Sep. 17, 2022 in U.S. Appl. No. 16/774,835, Feldman, B., et al., filed Jan. 28, 2020, 21 pages.

Office Action mailed Dec. 21, 2022 in U.S. Appl. No. 16/774,909, Ouyang, T., et al., filed Jan. 28, 2020, 13 pages.

Office Action mailed Nov. 25, 2022 in U.S. Appl. No. 17/151,274, Oja, S., et al., filed Jan. 18, 2021, 13 pages.

(56) References Cited

OTHER PUBLICATIONS

Office Action mailed Mar. 2, 2023 in U.S. Appl. No. 16/774,835, 14 pages.
Office Action mailed Aug. 8, 2023 in U.S. Appl. No. 16/774,909, 15 pages.
Office Action mailed Nov. 16, 2022 in U.S. Appl. No. 16/774,841, 11 pages.
D'Allegro, Joe, "Soon Your Car Will Know When You Are Having a Heart Attack—and Know How to React", CNBC, Nov. 17, 2017, https://www.cnbc.com/2017/11/17/cars-will-know-when-youre-having-a-beart-attack-and-how-to-react.html. Accessed Jul. 29, 2023.
Burmeister, J.J., and Gerhardt, G.A., "Self-referencing ceramic-based multisite microelectrodes for the detection and elimination of interferences from the measurement of L-glutamate and other analytes," Anal. Chem. 73(5):1037-1042, American Chemical Society, United States (Mar. 2001).
Mueller, S., et al., "The GOX/CAT system: a novel enzymatic method to independently control hydrogen peroxide and hypoxia in cell culture," Adv. Med. Sci. 54(2):121-135, Elsevier, Netherlands (2009).
Shi, G., et al., "The study of Nafion/xanthine oxidase/Au colloid chemically modified biosensor and its application in the determination of hypoxanthine in myocardial cells in vivo," Analyst 127(3):396-400, Royal Society of Chemistry, United States (Mar. 2002).
Office Action mailed Sep. 12, 2023 in U.S. Appl. No. 16/774,835, 16 pages.
Notice of Allowance mailed Aug. 16, 2023 in U.S. Appl. No. 16/774,841, 8 pages.
Office Action mailed Sep. 7, 2023 in U.S. Appl. No. 17/151,274, 13 pages.
Office Action mailed Sep. 21, 2023 in U.S. Appl. No. 17/819,099, 24 pages.
Alva, S., et al., "Feasibility of Continuous Ketone Monitoring in Subcutaneous Tissue Using a Ketone Sensor," Journal of Diabetes Science and Technology 15(4):768-774, Sage, United States (Jul. 2021).
D'Allegro, J., "Soon your car will know when you are having a heart attack and know how to react," Modem Medicine, CNBC, Accessed at https://www.cnbc.com/2017/11/17/cars-will-know-when-youre-having-a-heart-attack-and-how-to-react.html, Accessed on Oct. 10, 2023, (Nov. 17, 2017), 4 Pages.
Del Cano, R., et al., Ketone Bodies Detection: Wearable and Mobile Sensors for Personalized Medicine an Nutrition, Trends in Analytical Chemistry 159:116938, (Feb. 2023), 11 pages.
Final Office Action for U.S. Appl. No. 17/138,477, mailed on Apr. 3, 2024, 12 pages.
Final Office Action for U.S. Appl. No. 17/138,477, mailed on Mar. 17, 2023, 12 pages.
Final Office Action for U.S. Appl. No. 17/403,258, mailed on Nov. 13, 2024, 11 pages.
Final Office Action for U.S. Appl. No. 17/818,143 mailed on Jul. 30, 2024, 11 pages.
Final Office Action for U.S. Appl. No. 17/818,770 mailed on Jul. 30, 2024, 13 pages.
Final Office Action for U.S. Appl. No. 16/081,162, mailed on Dec. 30, 2020, 12 pages.
Final Office Action for U.S. Appl. No. 17/818,912, mailed on Oct. 25, 2024, 11 pages.
Final Office Action for U.S. Appl. No. 17/819,038, mailed on Aug. 26, 2024, 10 pages.
Franco, J.H., et al., "Product Analysis of Operating an Ethanol/O2 Biofuel Cell Shows the Synergy between Enzymes within an Enzymatic Cascade," Journal of The Electrochemical Society 165(9):H575-H579, (2018).
International Search Report and Written Opinion for PCT/US2017/020495, mailed on Jul. 10, 2017, 23 pages.
Kowalewska, B., and Kulesza, P.J., "Toward More Efficient Bioelectrocatalytic Oxidation of Ethanol for Amperometric Sensing and Biofuel Cell Technology," Analytical Chemistry 84(21):9564-9571, American Chemical Society, United States (Nov. 2012).
Nakabayashi, Y., et al., "Evaluation of Osmium(II) Complexes as Electron Transfer Mediators Accessible for Amperometric Glucose Sensors," Analytical Sciences 17(8):945-950, Springer, Switzerland (Aug. 2001).
Nikitina, O., et al., "Bi-enzyme Biosensor Based on NAD+- and Glutathione-dependent Recombinant Formaldehyde Dehydrogenase and Diaphorase for Formaldehyde Assay," Sensors and Actuators 125(1):1-9, (Jul. 2007).
Non-Final Office Action for U.S. Appl. No. 16/081,162 mailed on Jul. 22, 2020, 10 pages.
Non-Final Office Action for U.S. Appl. No. 17/138,477. mailed on Aug. 21, 2023, 12 pages.
Non-Final Office Action for U.S. Appl. No. 17/138,477, mailed on Sep. 12, 2022, 10 pages.
Non-Final Office Action for U.S. Appl. No. 17/403,258 mailed on Mar. 25, 2024, 9 pages.
Non-Final Office Action for U.S. Appl. No. 17/818,143 mailed on Jan. 24, 2024, 14 pages.
Non-Final Office Action for U.S. Appl. No. 17/818,143, mailed on Nov. 14, 2024, 12 pages.
Non-Final Office Action for U.S. Appl. No. 17/818,770 mailed on Mar. 12, 2024, 14 pages.
Non-Final Office Action for U.S. Appl. No. 17/818,770, mailed on Nov. 5, 2024, 14 pages.
Non-Final Office Action for U.S. Appl. No. 17/818,912 mailed on Apr. 26, 2024, 13 pages.
Non-Final Office Action for U.S. Appl. No. 17/819,038 mailed on Jan. 31, 2024, 11 pages.
Non-Final Office Action for U.S. Appl. No. 17/819,151 mailed on May 7, 2024, 13 pages.
Non-Final Office Action for U.S. Appl. No. 18/068,704 mailed on Dec. 16, 2025; 49 pages.
Non-Final Office Action for U.S. Appl. No. 18/597,704 mailed on Sep. 16, 2024, 09 pages.
Non-Final Office Action for U.S. Appl. No. 19/320,168, mailed on Dec. 15, 2025, 8 pages.
Non-Final Office Action for U.S. Appl. No. 19/320,172 mailed on Dec. 4, 2025; 10 pages.
Non-Final Office Action for U.S. Appl. No. 19/320,176 mailed on Dec. 3, 2025, 15 pages.
Non-Final Office Action for U.S. Appl. No. 19/320,180 mailed on Dec. 16, 2025; 17 pages.
Non-Final Office Action for U.S. Appl. No. 19/340,421 mailed on Nov. 28, 2025, 19 pages.
Non-Final Office Action for U.S. Appl. No. 19/340,445 mailed on Nov. 28, 2025, 20 pages.
Non-Final Office Action for U.S. Appl. No. 19/340,458 mailed on Nov. 28, 2025, 22 pages.
Notice of Allowance for U.S. Appl. No. 16/081,162, mailed on Apr. 13, 2021, 7 pages.
Notice of Allowance for U.S. Appl. No. 16/774,835 mailed on Jan. 20, 2026, 9 pages.
Notice of Allowance for U.S. Appl. No. 17/818,143, mailed on Jan. 21, 2026, 8 pages.
Notice of Allowance for U.S. Appl. No. 17/818,143 mailed on Oct. 28, 2025; 7 pages.
Notice of Allowance for U.S. Appl. No. 17/819,151, mailed on Oct. 22, 2024, 7 pages.
Notice of Allowance for U.S. Appl. No. 18/068,072, mailed on Jan. 23, 2026, 5 pages.
Notice of Allowance for U.S. Appl. No. 18/068,860, mailed on Jan. 22, 2026, 5 pages.
Notice of Allowance for U.S. Appl. No. 18/596,447, mailed on Jan. 21, 2026, 8 pages.
Notice of Allowance for U.S. Appl. No. 18/597,704 mailed on Jan. 27, 2026, 7 pages.
Pickup, J.C., "Glucose Sensors: Present and Future," International Textbook of Diabetes Mellitus, Third Edition, Defronzo, R.A., eds., 2:1686-1694, John Wiley & Sons Inc., United States (2004), 13 Pages.
Zhang, J.Y., et al., "Continuous Ketone Monitoring: A New Paradigm for Physiologic Monitoring," Journal of Diabetes Science and Technology 15(4):775-780, Sage, United States (Jul. 2021).

(56) References Cited

OTHER PUBLICATIONS

Final Office Action for U.S. Appl. No. 16/774,909 mailed on Apr. 9, 2024, 13 pages.
International Search Report and Written Opinion for International Application No. PCT/US2020/015365, mailed May 28, 2020, 14 pages.
International Search Report and Written Opinion for International Application No. PCT/US2020/015400, mailed on Apr. 9, 2020, 14 pages.
International Search Report and Written Opinion for International Application No. PCT/US2020/015321, mailed on Apr. 9, 2020, 14 pages.
Non-Final Office Action for U.S. Appl. No. 16/774,835 mailed on Apr. 15, 2024, 16 pages.
Non-Final Office Action for U.S. Appl. No. 17/819,099 mailed on Mar. 5, 2024, 14 pages.
Non-Final Office Action for U.S. Appl. No. 18/068,019 mailed on Feb. 29, 2024, 12 pages.
Non-Final Office Action for U.S. Appl. No. 18/068,072 mailed on Feb. 15, 2024, 13 pages.
Non-Final Office Action for U.S. Appl. No. 18/068,077 mailed on Jul. 30, 2024, 14 pages.
Non-Final Office Action for U.S. Appl. No. 18/068,704 mailed on Jun. 18, 2024, 14 pages.
Non-Final Office Action for U.S. Appl. No. 18/068,714 mailed on Mar. 5, 2024, 14 pages.
Non-Final Office Action for U.S. Appl. No. 18/068,834 mailed on Jan. 31, 2024, 10 pages.
Non-Final Office Action for U.S. Appl. No. 18/068,860 mailed on Jul. 15, 2024, 13 pages.
Notice of Allowance for U.S. Appl. No. 17/151,274 mailed on Feb. 7, 2024, 8 pages.
Final Office Action for U.S. Appl. No. 16/774,835 mailed on Dec. 24, 2024, 25 pages.
Notice of Allowance for U.S. Appl. No. 16/774,909 mailed on Sep. 29, 2024, 10 pages.
Notice of Allowance for U.S. Appl. No. 16/774,909 mailed on Dec. 27, 2024, 7 pages.
Final Office Action for U.S. Appl. No. 18/068,072 mailed on Oct. 18, 2024, 13 pages.
Final Office Action for U.S. Appl. No. 18/068,077 mailed on Jan. 28, 2025, 26 pages.
Final Office Action for U.S. Appl. No. 18/068,019 mailed on Oct. 17, 2024, 17 pages.
Final Office Action for U.S. Appl. No. 18/068,704 mailed on Jan. 24, 2025, 16 pages.
Final Office Action for U.S. Appl. No. 18/068,714 mailed on Oct. 18, 2024, 15 pages.
Final Office Action for U.S. Appl. No. 18/068,860 mailed on Oct. 18, 2024, 15 pages.
Non-Final Office Action for U.S. Appl. No. 18/068,834 mailed on Oct. 18, 2024, 15 pages.
Non-Final Office Action for U.S. Appl. No. 18/068,807 mailed on Jan. 29, 2025, 25 pages.
Notice of Allowance for U.S. Appl. No. 16/774,841 mailed on Feb. 9, 2024, 3 pages.
Notice of Allowance for U.S. Appl. No. 17/819,099 mailed on Jul. 9, 2024, 8 pages.

* cited by examiner

ANALYTE SENSORS AND SENSING METHODS FOR DETECTING CREATININE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental conditions. While a single analyte may be singularly dysregulated for a given physiological condition, it is sometimes the case that multiple analytes are concurrently dysregulated, either due to the same physiological condition or resulting from a comorbid (related) physiological condition. When multiple analytes are concurrently dysregulated, the extent of dysregulation may vary for each analyte. As such, each analyte may need to be monitored to obtain a satisfactory evaluation of an individual's health.

Periodic, ex vivo analyte monitoring using a withdrawn bodily fluid can be sufficient to observe a given physiological condition for many individuals. However, ex vivo analyte monitoring may be inconvenient or painful for some persons, particularly if bodily fluid withdrawal or collection needs to occur fairly frequently (e.g., several times per day). Continuous analyte monitoring using an implanted in vivo analyte sensor may be a more desirable approach for individuals having severe analyte dysregulation and/or rapidly fluctuating analyte levels, although it can also be beneficial for other individuals as well due to the convenience offered. Continuous analyte monitoring may allow an individual or physician to proactively address abnormal analyte levels before they have an opportunity to lead to more significant health consequences, such as organ damage or failure. Subcutaneous, interstitial, or dermal analyte sensors can provide sufficient measurement accuracy for this purpose in many cases while affording minimal user discomfort.

Many analytes represent intriguing targets for physiological analyses, provided that a suitable detection chemistry can be identified. To this end, amperometric sensors configured for assaying glucose in vivo have been developed and refined over recent years to aid in monitoring the health of diabetic individuals. Other analytes commonly subject to concurrent dysregulation with glucose in diabetic individuals include, for example, lactate, oxygen, pH, A1c, ketones, and the like. Sensors configured for detecting analytes commonly dysregulated in combination with glucose are known but are considerably less refined at present.

In vivo analyte sensors typically are configured to analyze for a single analyte in order to provide specific analyses, oftentimes employing an enzyme to provide high specificity for a given analyte. Because of such analytical specificity, current in vivo analyte sensors configured for assaying glucose are generally ineffective for assaying other analytes that are frequently dysregulated in combination with glucose or resulting from dysregulated glucose levels. At best, current analyte monitoring approaches require a diabetic individual to wear two different in vivo analyte sensors, one configured for assaying glucose and the other configured for assaying another analyte of interest. Analyte monitoring approaches employing multiple in vivo analyte sensors may be highly inconvenient for a user. Moreover, when multiple in vivo analyte sensors are used for analyte monitoring, there is an added cost burden for equipment and an increased statistical likelihood for failure of at least one of the individual in vivo analyte sensors.

Diabetic individuals are often particularly susceptible to comorbid conditions, which may result from mismanagement of their insulin levels or even as a consequence of having well-managed diabetes over a long period of time. By way of example, diabetic neuropathy may result from high blood glucose levels and lead to eventual kidney failure. Diabetic neuropathy is the leading cause of kidney failure in the United States and is experienced by a significant number of diabetic individuals within the first 10-20 years of their disease. Diagnostic tests for evaluating kidney function are currently based upon measurement of elevated creatinine levels in blood and/or urine samples. Although it is desirable to detect potential kidney failure as soon as possible, current diagnostic testing approaches are usually conducted over an extended period of time (months to years) to verify that creatinine levels are persistently increased or are trending upward over time. The infrequency of conventional creatinine monitoring may increase the risk of kidney failure occurring if abnormal kidney function is not detected early enough.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
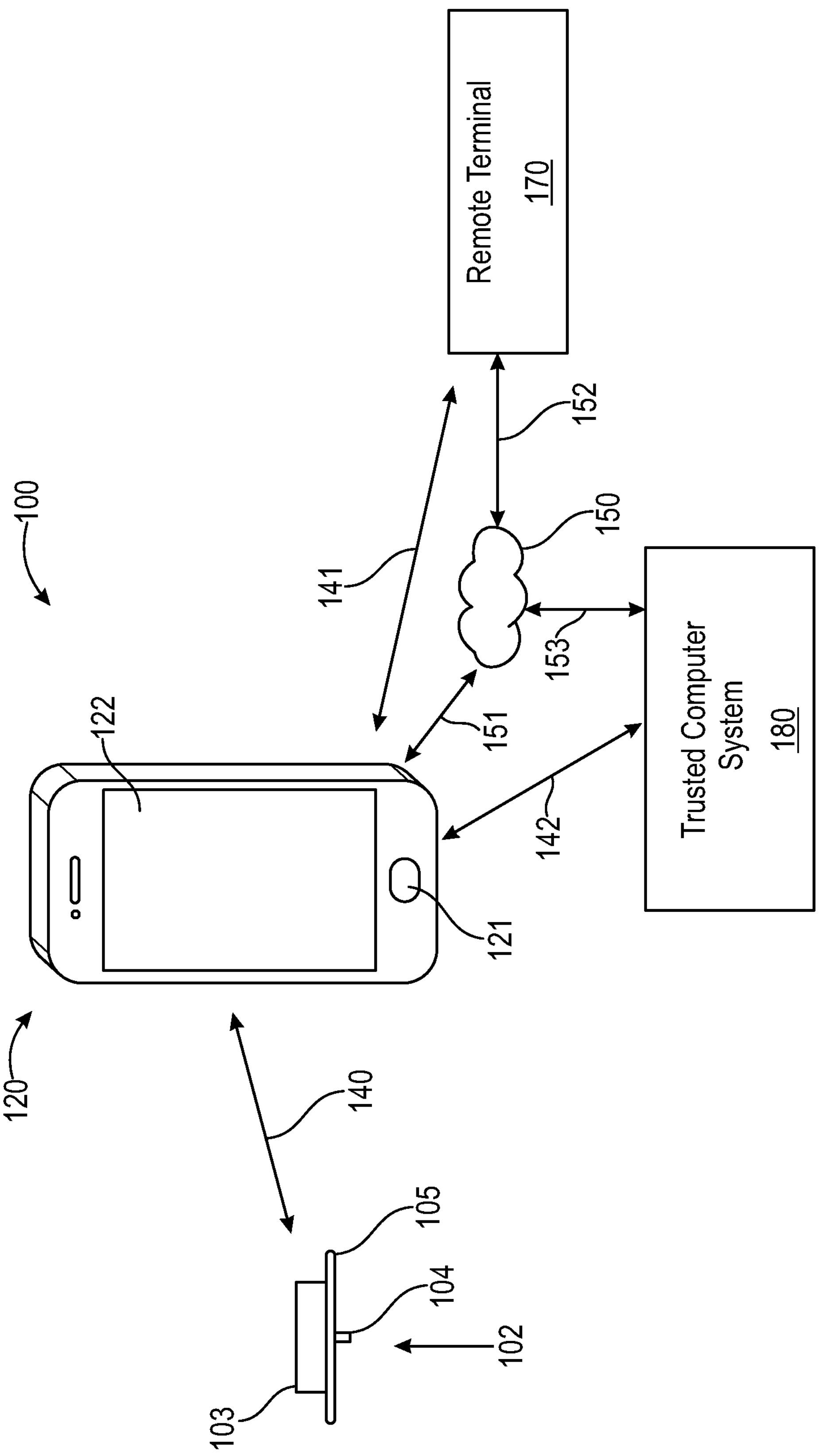
FIG. 1 shows a diagram of an illustrative sensing system that may incorporate an analyte sensor of the present disclosure.

The present disclosure generally describes analyte sensors employing multiple enzymes for detection of one or more analytes and, more specifically, analyte sensors employing multiple enzymes for detection of at least creatinine and, optionally, other analytes and corresponding methods for use thereof.

As discussed above, analyte sensors employing an enzyme are commonly used to monitor a single analyte, such as glucose, due to the enzyme's frequent specificity for a particular substrate or class of substrate. Other analytes may be monitored as well, provided that a suitable detection chemistry can be identified. The monitoring of multiple analytes may be complicated by the need to employ a corresponding number of analyte sensors to detect each analyte separately. This approach may be problematic or undesirable, especially when monitoring multiple analytes in vivo, due to issues such as, for example, the cost of multiple analyte sensors, user discomfort when wearing multiple analyte sensors, and an increased statistical likelihood for failure of an individual analyte sensor.

Glucose-responsive analyte sensors are a well-studied and still developing field to aid diabetic individuals in better managing their health. Despite the prevalence of comorbid conditions in diabetic individuals, sensor chemistries suitable for in vivo monitoring of other analytes commonly dysregulated in combination with glucose have significantly lagged behind the more well-developed glucose detection chemistry. Creatinine, for example, may be an analyte of particular interest for monitoring in individuals susceptible to kidney failure, particularly in diabetic individuals at risk for diabetic neuropathy.

The present disclosure provides analyte sensors that are responsive to creatinine. Specifically, the present disclosure provides analyte sensors that are capable of being worn on-body for in vivo monitoring of creatinine levels continuously or near-continuously. Analysis of creatinine levels with the analyte sensors disclosed herein may provide an individual or health care provider a more accurate representation of kidney function over an extended period of time than is possible with periodic, ex vivo laboratory measurements. By analyzing creatinine levels according to the present disclosure, earlier health care intervention may be possible to limit potential kidney damage and improve overall health outcomes for an individual.

Electrochemical detection of creatinine using a single enzymatic reaction is not feasible, since there is no known enzyme that is capable of transferring electrons directly from creatinine to a working electrode. The present disclosure alleviates this deficiency by providing sensor chemistries suitable for detecting creatinine with good response stability over a range of creatinine concentrations. In particular, the present disclosure utilizes enzyme systems comprising multiple enzymes that are capable of acting in concert to facilitate detection of creatinine. As used herein, the term "in concert" refers to a coupled enzymatic reaction, in which the product of a first enzymatic reaction becomes the substrate for a second enzymatic reaction, and the second enzymatic reaction serves as the basis for measuring the concentration of the substrate (analyte) reacted during the first enzymatic reaction. Although defined in terms of two coupled enzymatic reactions, it is to be appreciated that more than two enzymatic reactions may be coupled in some instances. For example, the product of a first enzymatic reaction may become the substrate of a second enzymatic reaction, and the product of the second enzymatic reaction may become the substrate for a third enzymatic reaction, with the third enzymatic reaction serving as the basis for measuring the concentration of the substrate (analyte) reacted during the first enzymatic reaction. As discussed further hereinbelow, suitable enzyme systems for detecting creatinine according to the present disclosure employ three enzymes acting in concert, along with a fourth enzyme or other oxygen scavenger to promote oxygen clearance. The fourth enzyme or other oxygen scavenger does not directly participate in the concerted enzymatic reactions but instead prevents an unwanted side reaction with oxygen from occurring.

It may be desirable to utilize two or more enzymes acting in concert with one another to detect an analyte of interest when a single enzyme is unable to facilitate detection, as is the case with creatinine. Situations in which a single enzyme may be ineffective for facilitating analyte detection include, for example, those in which the enzyme is inhibited by one or more reaction products, is unable to cycle between an oxidized state and reduced state when disposed in an analyte sensor, and/or is unknown for promoting a desired reaction pathway needed for detection. In the case of creatinine, the enzymatic conversion of creatinine into creatine occurs hydrolytically and does not result in a change of oxidation state to provide a current to a working electrode for promoting detection of this analyte. An enzyme system containing multiple enzymes acting in concert according to the disclosure herein may alleviate this difficulty.

The creatinine sensors disclosed herein may be advantageous for monitoring creatinine levels (and kidney function) in any individual potentially at risk for kidney damage or failure, but they may be particularly beneficial for diabetic individuals due to the prevalence of diabetic neuropathy. Although it may be beneficial to monitor creatinine levels alone, it is also possible for a diabetic individual to monitor both their glucose and creatinine levels to afford improved health outcomes, particularly given that glucose monitoring is already performed routinely by diabetic individuals. The present disclosure provides for monitoring of both glucose and creatinine using one or more in vivo analyte sensors responsive to each analyte, and in particularly advantageous configurations, a single analyte sensor that is responsive to both analytes in vivo may be used. Advantageously and surprisingly, analyte sensors incorporating sensing functionality for both glucose and creatinine upon a single sensor tail may be fabricated by employing the disclosure herein.

As discussed further hereinbelow in reference to FIGS. 2A and 2B, a creatinine-responsive active area of the present disclosure may utilize an oxygen scavenger to facilitate detection of creatinine using the enzyme system shown therein. Oxidase enzymes may serve as the oxygen scavenger in certain sensor configurations. Glucose oxidase may be a particularly advantageous oxygen scavenger, since glucose is widely present in bodily fluids also containing creatinine, in which case the glucose may serve as a reagent for clearing oxygen (see Reaction 1 below). The oxygen scavenger may be electrically isolated from the creatinine-responsive active area by a membrane, so as not to generate a signal at the working electrode bearing the creatinine-responsive active area (i.e., upon clearing oxygen by promoting an oxidation reaction). The oxygen scavenger may be located upon the membrane in order to promote effective oxygen scavenging within the creatinine-responsive active area. In addition to being disposed upon the membrane, the oxygen scavenger may be located at a second location upon the sensor tail remote from the membrane, wherein the remote oxygen scavenger may function differently at the remote location (e.g., by promoting detection of glucose in a glucose-responsive active area). Depending on how and where the remote oxygen scavenger is disposed, the oxygen scavenger may be active or inactive for promoting detection of another analyte, particularly glucose, in addition to its oxygen clearing function. When inactive for promoting detection of glucose, glucose oxidase may be electrically isolated from a working electrode, such that the oxidation reaction (oxygen clearing) promoted by this enzyme does not lead to current generation at the working electrode. When the glucose oxidase is active both for promoting glucose detection and for clearing oxygen, the glucose oxidase may be present in a glucose-responsive active area that is either disposed on a second working electrode or positioned on the working electrode bearing the creatinine-responsive active area such that separate signals may be obtained from each. Strategies for disposing both a creatinine-responsive active area and a glucose-responsive active area upon a single sensor tail are discussed further hereinbelow.

Even with suitable detection chemistries in hand, incorporating two different types of active areas upon a single analyte sensor is sometimes not a straightforward matter. Analyte sensors oftentimes employ a membrane overcoating the active area(s) to function as a mass transport limiting membrane and/or to improve biocompatibility. Limiting analyte access to the active area(s) with a mass transport limiting membrane can aid in avoiding sensor overload (saturation), thereby improving detection performance and accuracy. When assaying multiple analytes using a single analyte sensor, different permeability values may be exhibited by the various analytes across a given mass transport limiting membrane, potentially resulting in widely disparate sensitivities for each analyte. Incorporating different mass transport limiting membranes upon each active area may be problematic in some instances. Surprisingly and advantageously, glucose and creatinine may be successfully analyzed using a mass transport limiting membrane that is compositionally the same at each location, thereby simplifying fabrication of analyte sensors having detection capabilities for both analytes.

Before describing the analyte sensors of the present disclosure in further detail, a brief overview of suitable in vivo analyte sensor configurations and sensor systems employing the analyte sensors will be provided first so that the embodiments of the present disclosure may be better understood. FIG. 1 shows a diagram of an illustrative sensing system that may incorporate an analyte sensor of the present disclosure, specifically an analyte sensor comprising a creatinine-responsive active area and optionally a glucose-responsive active area. As shown, sensing system 100 includes sensor control device 102 and reader device 120 that are configured to communicate with one another over a local communication path or link, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer system 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 and incorporated herein by reference in its entirety. Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise at least one working electrode and a creatinine-responsive active area disposed thereon. Optionally, a glucose-responsive active area, further optionally in combination with a second working electrode, may be located upon the sensor tail to facilitate detection of this analyte. A counter electrode may be present in combination with the at least one working electrode. Particular electrode configurations upon the sensor tail are described in more detail below in reference to FIGS. 3A-7B.

At least one mass transport limiting membrane may overcoat the creatinine-responsive active area and the optional glucose-responsive active area, when present, as also described in further detail below. The glucose-responsive active area, when present, may comprise a glucose-responsive enzyme. The mass transport limiting membrane may also overcoat the oxygen scavenger (e.g., glucose oxidase), in which case the oxygen scavenger may be interposed between separate membrane layers.

The creatinine-responsive active area may comprise an enzyme system comprising multiple enzymes that are capable of acting in concert to facilitate detection of creatinine, as described below in reference to FIGS. 2A and 2B. The creatinine-responsive active area and, when present, the glucose-responsive active area may include a polymer to which the enzymes are covalently bonded, according to various embodiments. Glucose oxidase disposed outside of a glucose-responsive active area may also be covalently bonded to a polymer in the analyte sensors disclosed herein. According to the present disclosure, creatinine and, optionally, glucose may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid to determine concentrations of creatinine and/or glucose in vivo.

Referring still to FIG. 1, sensor 104 may automatically forward data to reader device 120. For example, analyte concentration data (i.e., creatinine and/or glucose concentrations) may be communicated automatically and periodically, such as at a certain frequency as data is obtained or after a certain time period has passed, with the data being stored in a memory until transmittal (e.g., every minute, five minutes, or other predetermined time period). In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a user does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle is subsequently withdrawn after facilitating sensor insertion.

Figure 2A:
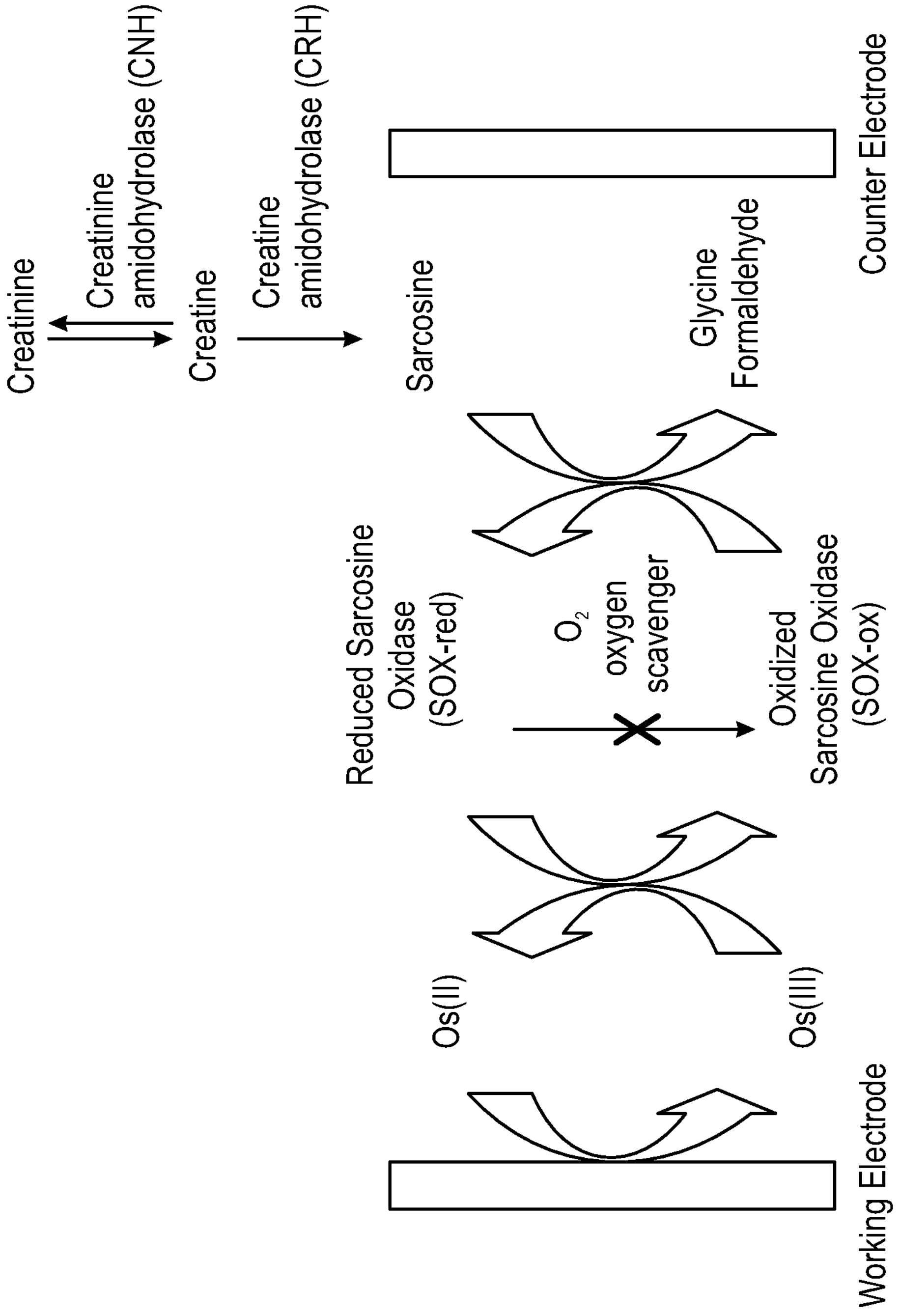
FIGS. 2A and 2B show an example of a concerted enzyme system that may be used for detecting creatinine according to the present disclosure.
Figure 2B:
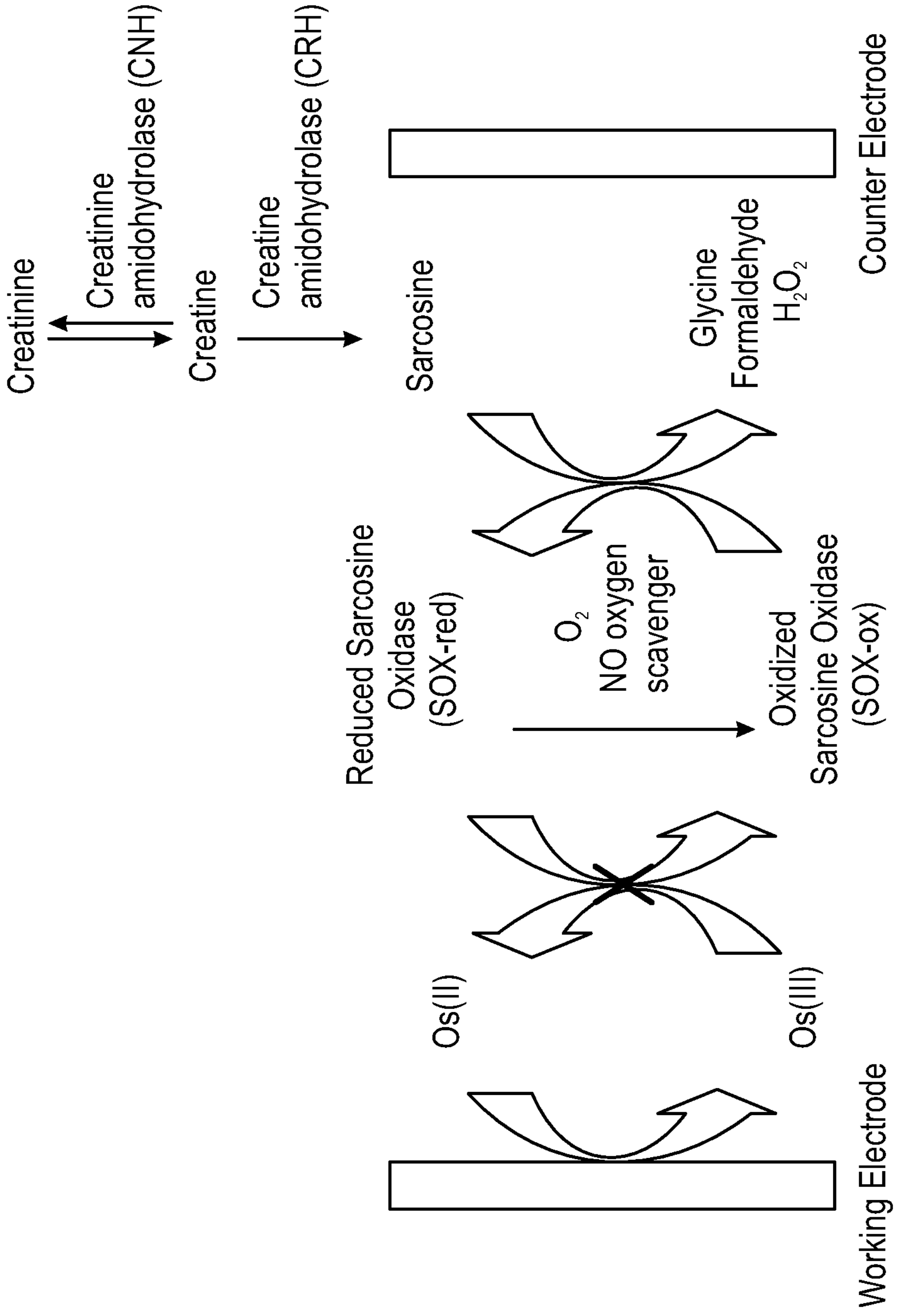

A suitable enzyme system that may be used for detecting creatinine according to the disclosure herein is described in further detail in reference to FIGS. 2A and 2B. As shown, creatinine may react reversibly and hydrolytically in the presence of creatinine amidohydrolase (CNH) to form creatine. Creatine, in turn, may undergo catalytic hydrolysis in the presence of creatine amidinohydrolase (CRH) to form sarcosine. Neither of these reactions produces a flow of electrons (e.g., oxidation or reduction) to provide a basis for electrochemical detection of the creatinine.

As further shown in FIGS. 2A and 2B, the sarcosine produced via hydrolysis of creatine may undergo oxidation in the presence of the oxidized form of sarcosine oxidase (SOX-ox) to form glycine and formaldehyde, thereby generating the reduced form of sarcosine oxidase (SOX-red) in the process. Hydrogen peroxide also may be generated in the presence of oxygen (FIG. 2B). The reduced form of sarcosine oxidase, in turn, may then undergo re-oxidation in the presence of the oxidized form of an electron transfer agent (e.g., Os(III)), thereby producing the corresponding reduced form of the electron transfer agent (e.g., Os(II)) and delivering a flow of electrons to the working electrode.

Oxygen may interfere with the concerted sequence of reactions used to detect creatinine according to the present disclosure. Specifically, as shown in FIG. 2B, the reduced form of sarcosine oxidase may undergo a reaction with oxygen to reform the corresponding oxidized form of this enzyme but without exchanging electrons with the electron transfer agent. Although the enzymes all remain active when the reaction with oxygen occurs, no electrons flow to the working electrode. Without being bound by theory or mechanism, the competing reaction with oxygen is believed to result from kinetic effects. That is, oxidation of the reduced form of sarcosine oxidase with oxygen is believed to occur faster than does oxidation promoted by the electron transfer agent. Hydrogen peroxide is also formed in the presence of the oxygen.

The desired reaction pathway for facilitating detection of creatinine is shown in FIG. 2A. Oxidation of the reduced form of sarcosine oxidase may be encouraged by including an oxygen scavenger in proximity to the enzyme system. As discussed above, various oxygen scavengers and dispositions thereof may be suitable, including oxidase enzymes such as glucose oxidase. Small molecule oxygen scavengers may also be suitable, but they may be fully consumed before the sensor lifetime is otherwise fully exhausted. Enzymes, in contrast, may undergo reversible oxidation and reduction, thereby affording a longer sensor lifetime. By discouraging oxidation of the reduced form of sarcosine oxidase with oxygen, the slower electron exchange reaction with the electron transfer agent may occur, thereby allowing a current to be produced at the working electrode. The magnitude of the current produced is proportional to the amount of creatinine that was initially reacted.

The oxygen scavenger used for encouraging the desired reaction pathway in FIG. 2A may be an oxidase enzyme in any embodiment of the present disclosure. Any oxidase enzyme may be used to promote oxygen scavenging in proximity to the enzyme system, provided that a suitable substrate for the enzyme is also present in a creatinine-containing fluid, thereby providing a reagent for reacting with the oxygen in the presence of the oxidase enzyme. Oxidase enzymes that may be suitable for oxygen clearing in the present disclosure include, but are not limited to, glucose oxidase, lactate oxidase, xanthine oxidase, and the like. Glucose oxidase may be a particularly suitable oxidase enzyme for use in the present disclosure due to the ready availability of glucose in various bodily fluids. Reaction 1 below shows the enzymatic reaction promoted by glucose oxidase to afford oxygen clearing.

$$\beta\text{-D-glucose}+O_2\rightarrow\text{D-glucono-1,5-lactone}+H_2O_2 \quad \text{Reaction 1}$$

The concentration of available lactate in vivo is lower than that of glucose, but still sufficient to promote oxygen scavenging.

Oxidase enzymes, such as glucose oxidase, may be positioned in any location suitable to promote oxygen scavenging in the analyte sensors disclosed herein. Glucose oxidase, for example, may be positioned upon the sensor tail such that the glucose oxidase is functional and/or non-functional for promoting glucose detection. When non-functional for promoting glucose detection, the glucose oxidase may be positioned upon the sensor tail such that electrons produced during glucose oxidation are precluded from reaching the working electrode that receives electrons generated upon oxidizing sarcosine. Approaches for electrically isolating the glucose oxidase from the working electrode are addressed in more detail below. When functional for promoting glucose detection, the glucose oxidase may be located in a glucose-responsive active area upon a working electrode, such that, in addition to scavenging oxygen in proximity to the creatinine-responsive active area, the electrons generated during glucose oxidation are received by the working electrode. The working electrode having a glucose-responsive active area thereon may be the same working electrode as the one bearing the creatinine-responsive active area or a different working electrode. Suitable approaches for disposing glucose oxidase within a glucose-responsive active area upon a particular working electrode are also discussed hereinbelow. Any combination of the foregoing approaches for disposing glucose oxidase upon the sensor tail may be used in the analyte sensors disclosed herein.

An alternative detection strategy to that depicted in FIG. 2A may omit the glucose oxidase, the membrane separating the glucose oxidase from the working electrode, and the electron transfer agent. In such a detection approach, creatinine amidohydrolase, creatine amidinohydrolase and sarcosine oxidase may operate in concert as depicted, with oxygen promoting formation of hydrogen peroxide and interconverting the oxidized and reduced forms of sarcosine oxidase. The hydrogen peroxide may be detected at the working electrode to serve as the basis for assaying creatinine in this type of sensor configuration.

The analyte sensors disclosed herein feature at least a creatinine-responsive active area upon a working electrode, in combination with at least one additional electrode, which may be a counter electrode, a reference electrode, and/or a counter/reference electrode. Analyte sensors featuring both a creatinine-responsive active area and a glucose-responsive active area may incorporate the creatinine-responsive active area and the glucose-responsive active area upon separate working electrodes or upon the same working electrode. Illustrative configurations for each possibility are discussed hereinbelow.

Figure 3A:
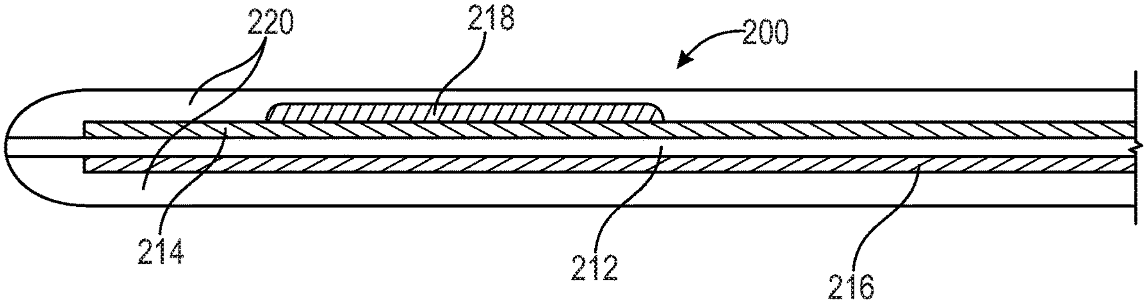
FIGS. 3A-3C show cross-sectional diagrams of illustrative analyte sensors having an active area suitable for detecting creatinine.
Figure 3B:
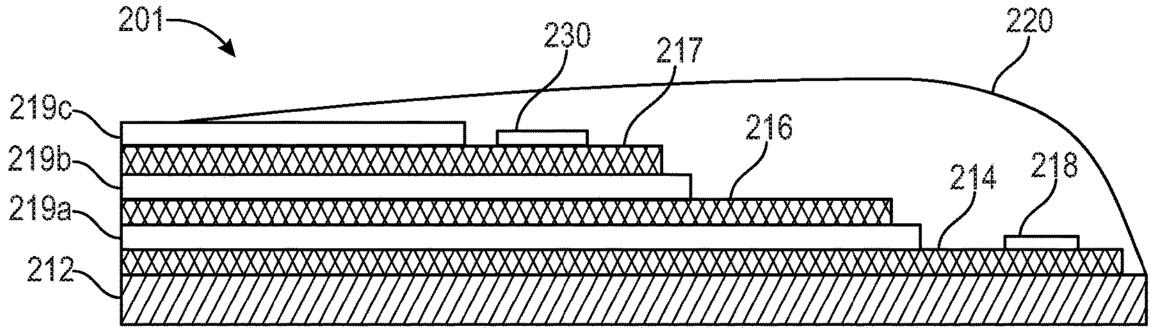
Figure 3C:
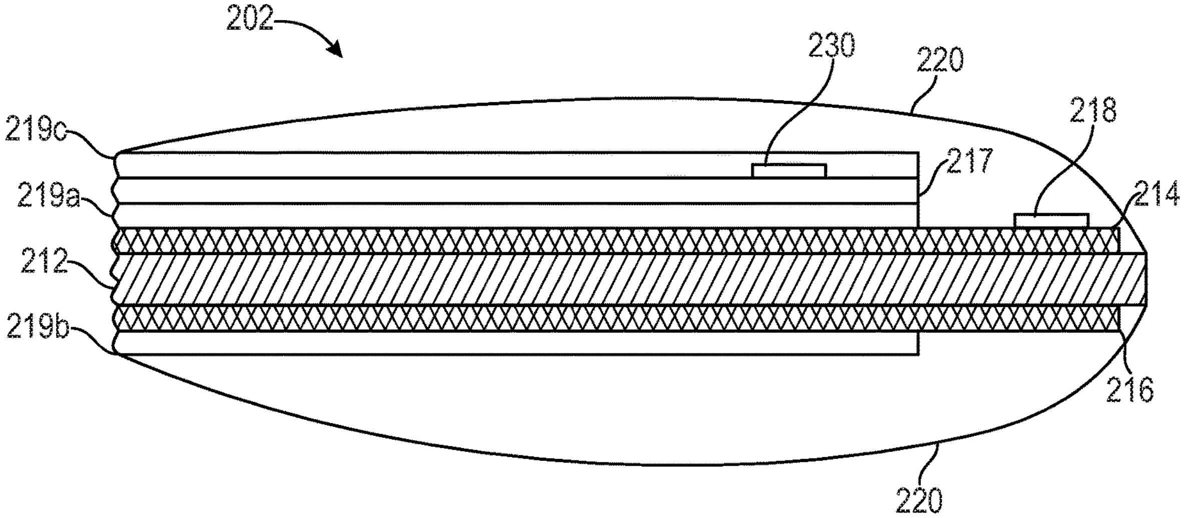

Sensor configurations featuring a creatinine-responsive active area but not a glucose-responsive active area may employ two-electrode or three-electrode detection motifs, as described further herein in reference to FIGS. 3A-3C.

Sensor configurations featuring both a creatinine-responsive active area and a glucose-responsive active area, either upon separate working electrodes or upon the same working electrode, are described separately thereafter in reference to FIGS. 4A-6C. Sensor configurations having multiple working electrodes may be particularly advantageous for incorporating both a creatinine-responsive active area and a glucose-responsive active area within the same sensor tail, since the signal contribution from each active area may be determined more readily.

When a single working electrode is present in an analyte sensor, three-electrode sensor configurations may comprise a working electrode, a counter electrode, and a reference electrode. Related two-electrode sensor configurations may comprise a working electrode and a second electrode, in which the second electrode may function as both a counter electrode and a reference electrode (i.e., a counter/reference electrode). The various electrodes may be at least partially stacked (layered) upon one another and/or laterally spaced apart from one another upon the sensor tail. Suitable sensor configurations may be substantially flat in shape or substantially cylindrical in shape, with the creatinine-responsive active area and the optional glucose-responsive active area being laterally spaced apart upon the working electrode. In any of the sensor configurations disclosed herein, the various electrodes may be electrically isolated from one another by a dielectric material or similar insulator.

Analyte sensors featuring multiple working electrodes may similarly comprise at least one additional electrode. When one additional electrode is present, the one additional electrode may function as a counter/reference electrode for each of the multiple working electrodes. When two additional electrodes are present, one of the additional electrodes may function as a counter electrode for each of the multiple working electrodes and the other of the additional electrodes may function as a reference electrode for each of the multiple working electrodes.

FIG. 3A shows a diagram of an illustrative two-electrode analyte sensor configuration, which is compatible for use in the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Creatinine-responsive active area 218 is disposed as at least one layer upon at least a portion of working electrode 214. Creatinine-responsive active area 218 may comprise multiple spots or a single spot configured for detection of creatinine, as discussed further herein.

Referring still to FIG. 3A, membrane 220 overcoats at least creatinine-responsive active area 218 and may optionally overcoat some or all of working electrode 214 and/or counter/reference electrode 216, or the entirety of analyte sensor 200, according to some embodiments. One or both faces of analyte sensor 200 may be overcoated with membrane 220. Membrane 220 may comprise one or more polymeric membrane materials having capabilities of limiting analyte flux to active area 218 (i.e., membrane 220 is a mass transport limiting membrane having some permeability for creatinine). The composition and thickness of membrane 220 may vary to promote a desired creatinine flux to creatinine-responsive active area 218, thereby providing a desired signal intensity and stability. Analyte sensor 200 may be operable for assaying creatinine by any of coulometric, amperometric, voltammetric, or potentiometric electrochemical detection techniques.

FIGS. 3B and 3C show diagrams of illustrative three-electrode analyte sensor configurations, which are also compatible for use in the disclosure herein. Three-electrode analyte sensor configurations may be similar to that shown for analyte sensor 200 in FIG. 3A, except for the inclusion of additional electrode 217 in analyte sensors 201 and 202 (FIGS. 3B and 3C). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219*a*, 219*b* and 219*c* separate electrodes 214, 216 and 217 from one another and provide electrical isolation. Alternately, at least one of electrodes 214, 216 and 217 may be located upon opposite faces of substrate 212, as shown in FIG. 3C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with sensor 200 shown in FIG. 3A, creatinine-responsive active area 218 in analyte sensors 201 and 202 may comprise multiple spots or a single spot. Additionally, analyte sensors 201 and 202 may be operable for assaying creatinine by any of coulometric, amperometric, voltammetric, or potentiometric electrochemical detection techniques.

Like analyte sensor 200, membrane 220 may also overcoat creatinine-responsive active area 218, as well as other sensor components, in analyte sensors 201 and 202, thereby serving as a mass transport limiting membrane. Additional electrode 217 may be overcoated with membrane 220 in some embodiments. Although FIGS. 3B and 2C have depicted all of electrodes 214, 216 and 217 as being overcoated with membrane 220, it is to be recognized that only working electrode 214 may be overcoated in some embodiments. Moreover, the thickness of membrane 220 at each of electrodes 214, 216 and 217 may be the same or different. As in two-electrode analyte sensor configurations (FIG. 3A), one or both faces of analyte sensors 201 and 202 may be overcoated with membrane 220 in the sensor configurations of FIGS. 3B and 3C, or the entirety of analyte sensors 201 and 202 may be overcoated. Accordingly, the three-electrode sensor configurations shown in FIGS. 3B and 3C should be understood as being non-limiting of the embodiments disclosed herein, with alternative electrode and/or layer configurations remaining within the scope of the present disclosure.

Analyte sensors having both a creatinine-responsive active area and a glucose-responsive active area upon a single working electrode or upon multiple working electrodes are described in further detail in reference to FIGS. 4A-6C.

Figure 4A:
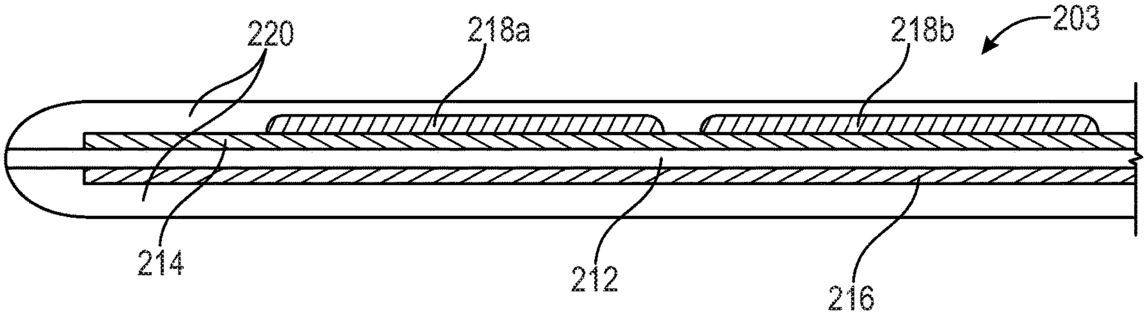
FIGS. 4A-4C show cross-sectional diagrams of illustrative analyte sensors having a single working electrode and active areas suitable for detecting creatinine and glucose.

FIG. 4A shows an illustrative configuration for sensor 203 having a single working electrode with both a creatinine-responsive active area and a glucose-responsive active area disposed thereon. FIG. 4A is similar to FIG. 3A, except for the presence of two active areas upon working electrode 214: creatinine-responsive active area 218*a* and glucose-responsive active area 218*b*, which are laterally spaced apart from one another upon the surface of working electrode 214. Active areas 218*a* and 218*b* may comprise multiple spots or a single spot configured for detection of each analyte. The composition of membrane 220 may vary or be compositionally the same at active areas 218*a* and 218*b*.

Figure 4B:
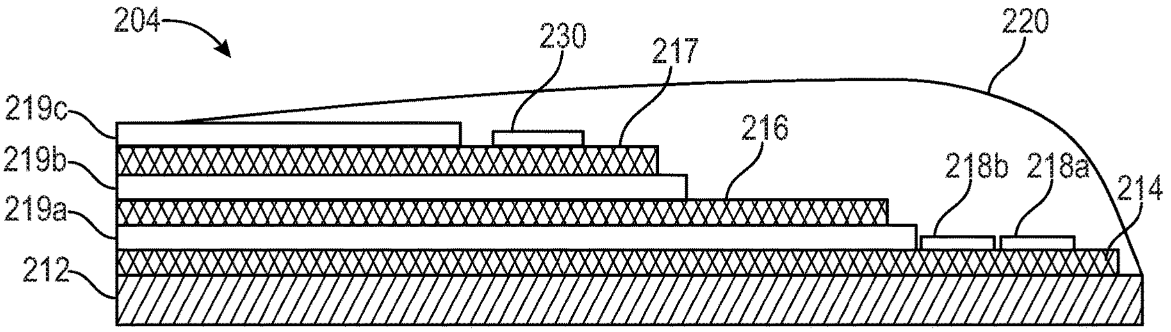
Figure 4C:
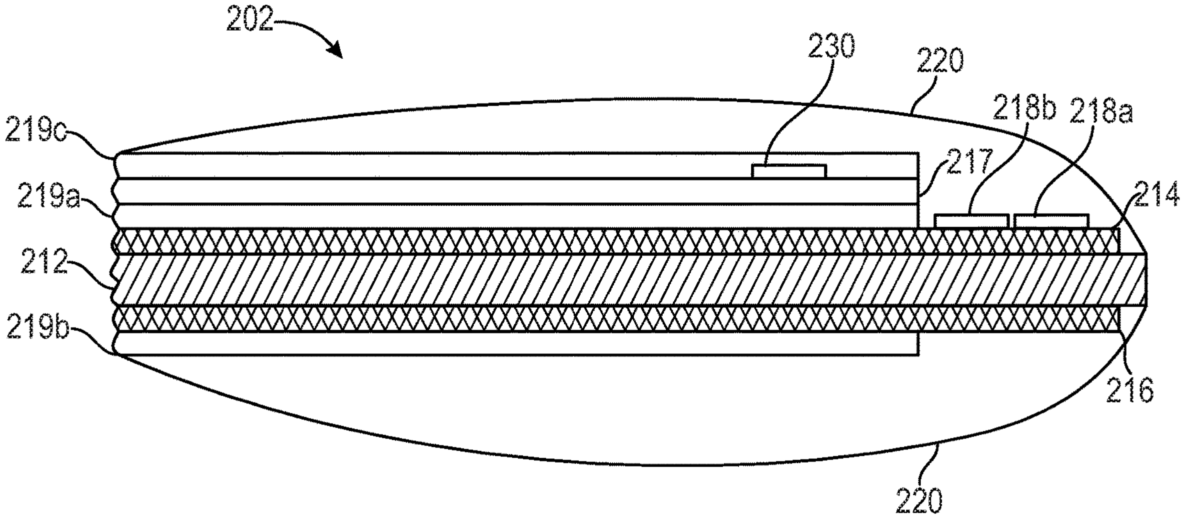

FIGS. 4B and 4C show cross-sectional diagrams of illustrative three-electrode sensor configurations for sensors 204 and 205, respectively, each featuring a single working electrode having both creatinine-responsive active area 218*a* and glucose-responsive active area 218*b* disposed thereon. FIGS. 4B and 4C are otherwise similar to FIGS. 3B and 3C and may be better understood by reference thereto. As with FIG. 4A, the composition of membrane 220 may vary or be compositionally the same at active areas 218*a* and 218*b*.

Figure 5:
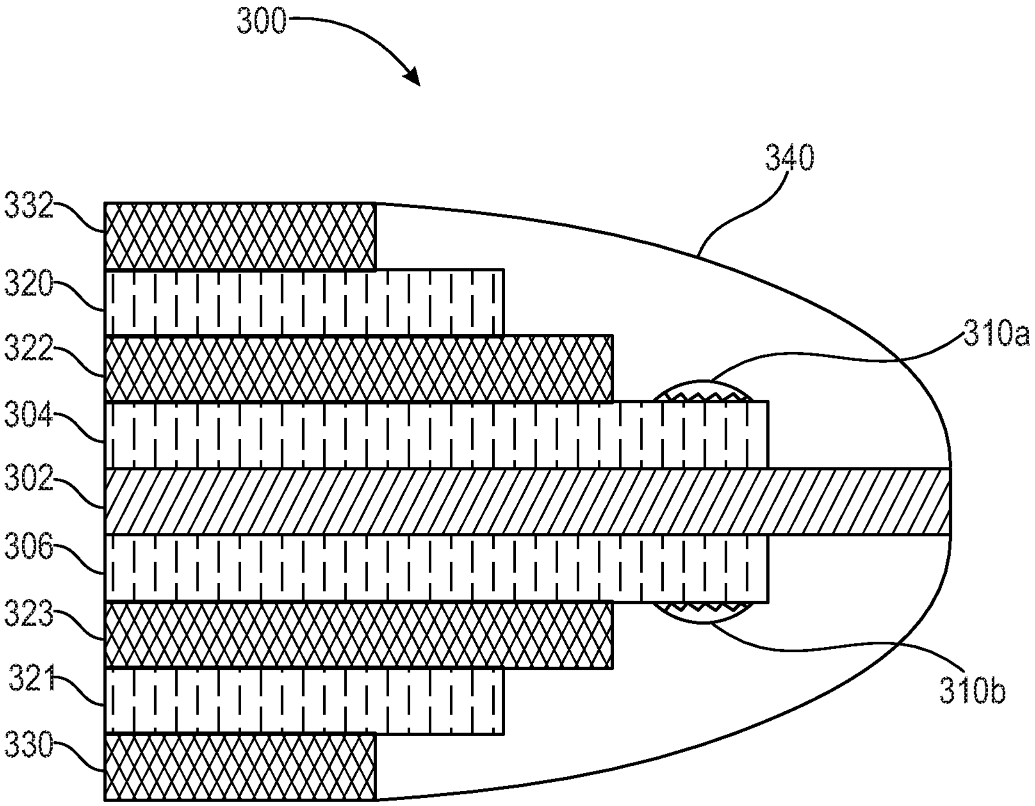
FIG. 5 shows a cross-sectional diagram of an illustrative analyte sensor having two working electrodes and active areas suitable for detecting creatinine and glucose.
Figure 6A:
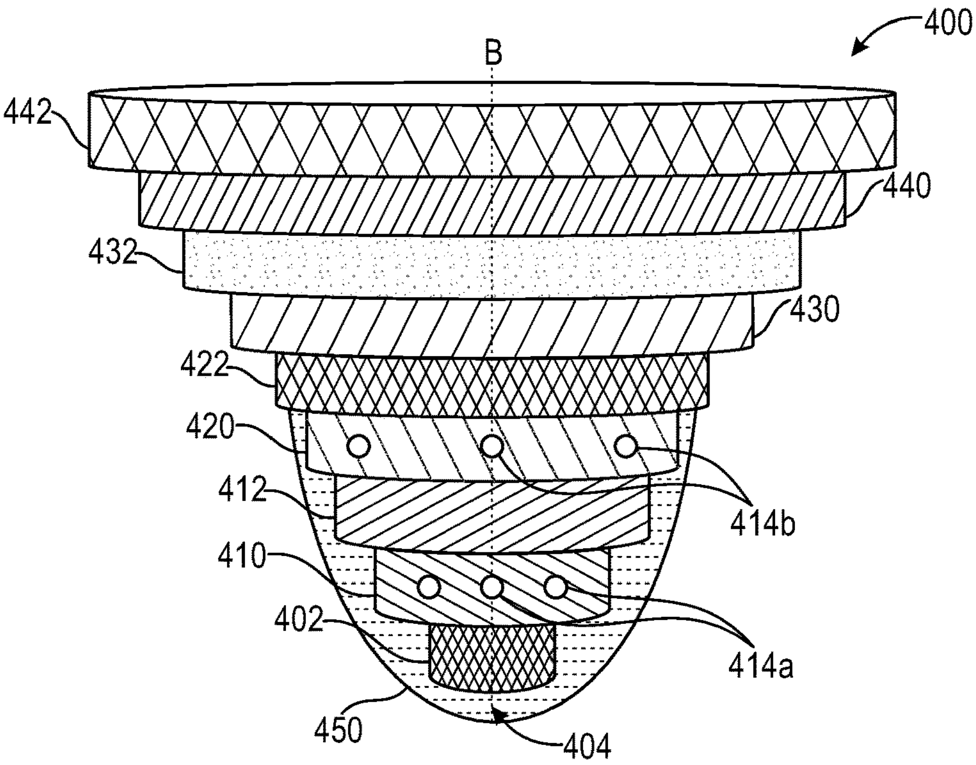
FIGS. 6A-6D show perspective views of illustrative analyte sensors featuring electrodes that are disposed concentrically with respect to one another.
Figure 6B:
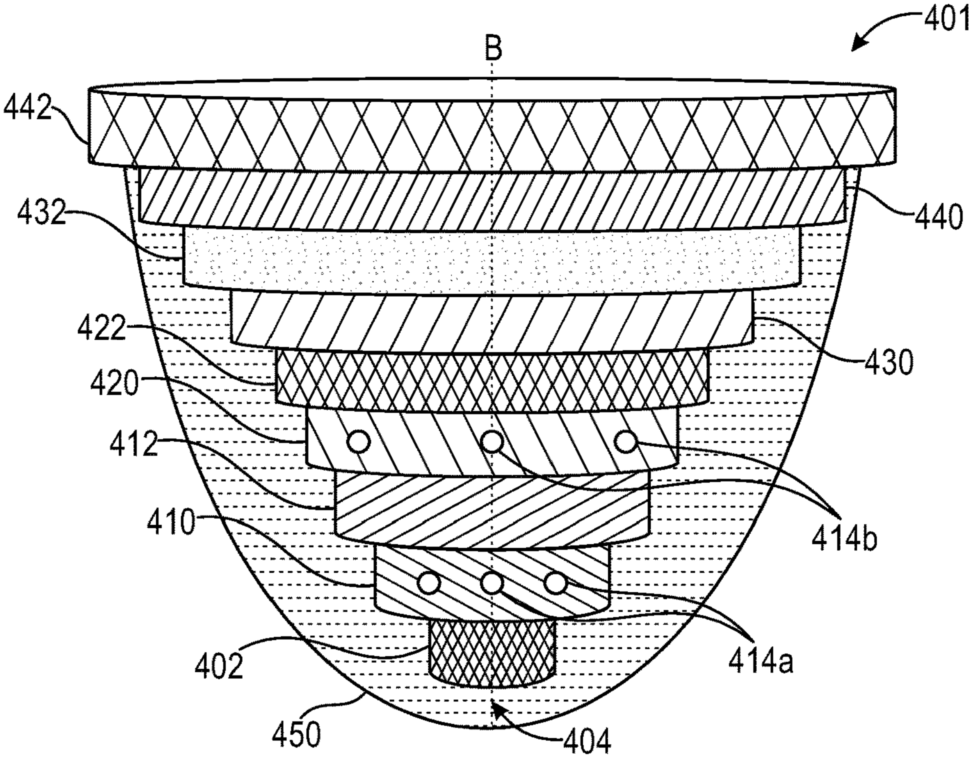
Figure 6C:
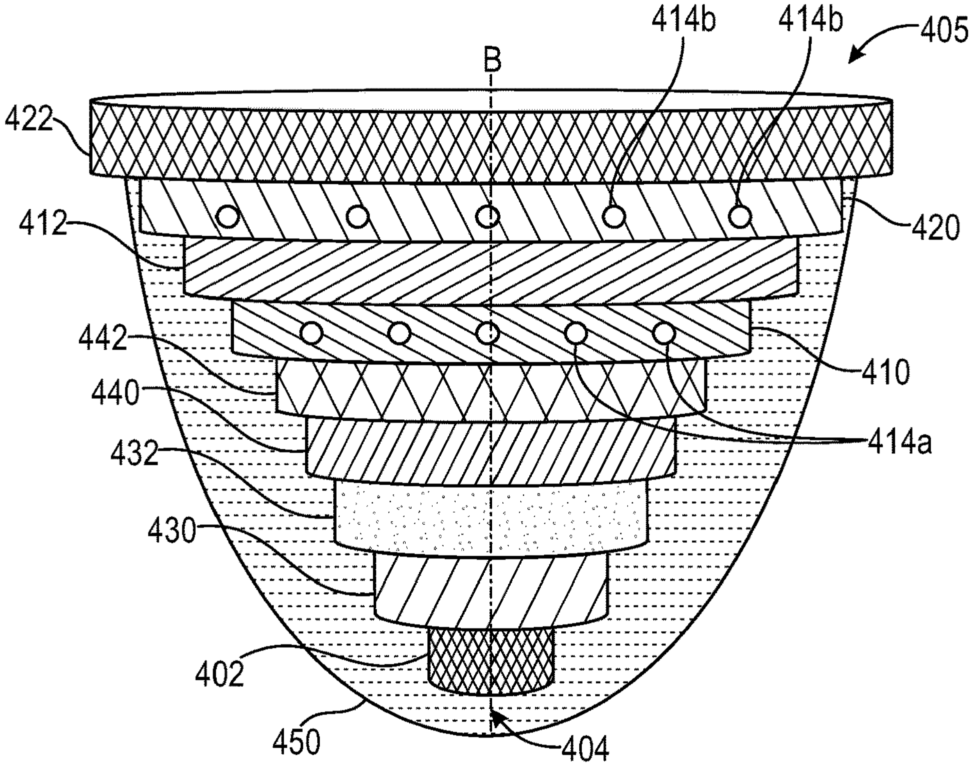
Figure 6D:
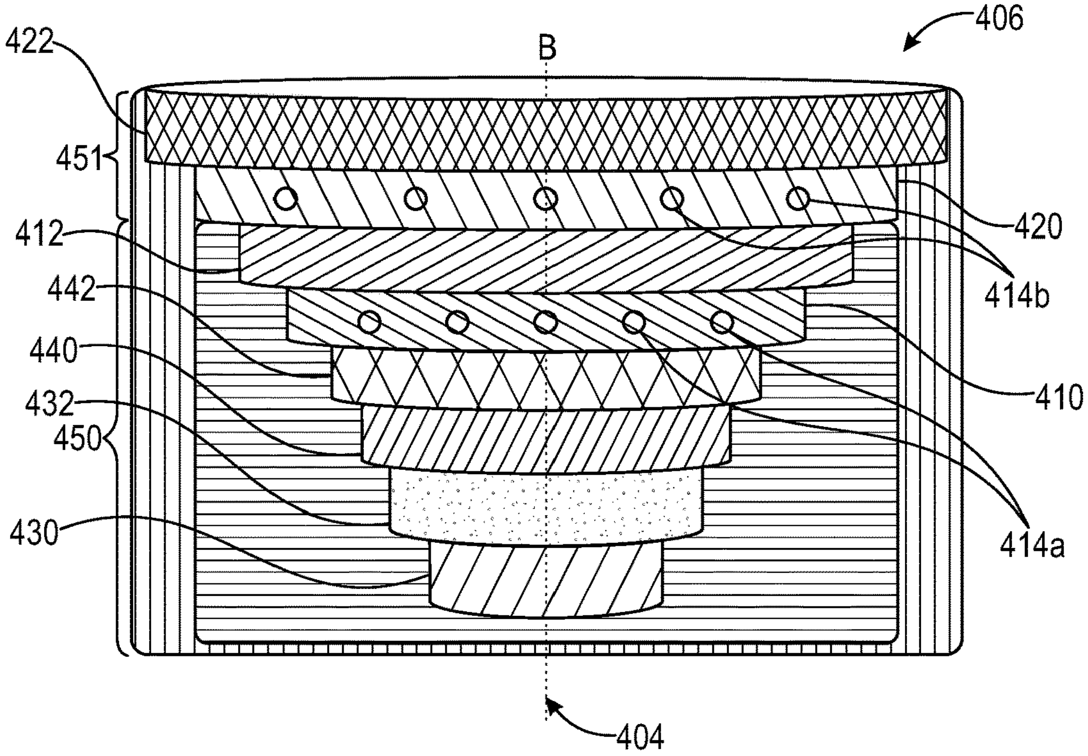

Illustrative sensor configurations having multiple working electrodes, specifically two working electrodes, are described in further detail in reference to FIGS. 5-6D. Although the following description is primarily directed to sensor configurations having two working electrodes, it is to be appreciated that more than two working electrodes may be incorporated through extension of the disclosure herein. Additional working electrodes may be used to impart additional sensing capabilities to the analyte sensors beyond just creatinine and glucose sensing.

FIG. 5 shows a cross-sectional diagram of an illustrative analyte sensor configuration having two working electrodes, a reference electrode and a counter electrode, which is compatible for use in the disclosure herein. As shown, analyte sensor 300 includes working electrodes 304 and 306 disposed upon opposite faces of substrate 302. Creatinine-responsive active area 310*a* is disposed upon the surface of working electrode 304, and glucose-responsive active area 310*b* is disposed upon the surface of working electrode 306. Counter electrode 320 is electrically isolated from working electrode 304 by dielectric layer 322, and reference electrode 321 is electrically isolated from working electrode 306 by dielectric layer 323. Outer dielectric layers 330 and 332 are positioned upon reference electrode 321 and counter electrode 320, respectively. Membrane 340 may overcoat at least active areas 310*a* and 310*b*, according to various embodiments, with other components of analyte sensor 300 or the entirety of analyte sensor 300 optionally being overcoated with membrane 340 as well. Again, membrane 340 may vary compositionally at active areas 310*a* and 310*b*, if needed, in order to afford suitable permeability values for differentially regulating the analyte flux at each location.

Alternative sensor configurations having multiple working electrodes and differing from the configuration shown in FIG. 5 may feature a counter/reference electrode instead of separate counter and reference electrodes 320,321, and/or feature layer and/or membrane arrangements varying from those expressly depicted. For example, the positioning of counter electrode 320 and reference electrode 321 may be reversed from that depicted in FIG. 5. In addition, working electrodes 304 and 306 need not necessarily reside upon opposing faces of substrate 302 in the manner shown in FIG. 4.

Although suitable sensor configurations may feature electrodes that are substantially planar in character, it is to be appreciated that sensor configurations featuring non-planar electrodes may be advantageous and particularly suitable for use in the disclosure herein. In particular, substantially cylindrical electrodes that are disposed concentrically with respect to one another may facilitate deposition of a mass transport limiting membrane, as described hereinbelow. FIGS. 6A-6D show perspective views of analyte sensors featuring two working electrodes that are disposed concentrically with respect to one another. It is to be appreciated that sensor configurations having a concentric electrode disposition but lacking a second working electrode are also possible in the present disclosure.

FIG. 6A shows a perspective view of an illustrative sensor configuration in which multiple electrodes are substantially cylindrical and are disposed concentrically with respect to one another about a central substrate. As shown, analyte sensor 400 includes central substrate 402 about which all electrodes and dielectric layers are disposed concentrically with respect to one another. In particular, working electrode 410 is disposed upon the surface of central substrate 402, and dielectric layer 412 is disposed upon a portion of working electrode 410 distal to sensor tip 404. Working electrode 420 is disposed upon dielectric layer 412, and dielectric layer 422 is disposed upon a portion of working electrode 420 distal to sensor tip 404. Counter electrode 430 is disposed upon dielectric layer 422, and dielectric layer 432 is disposed upon a portion of counter electrode 430 distal to sensor tip 404. Reference electrode 440 is disposed upon dielectric layer 432, and dielectric layer 442 is disposed upon a portion of reference electrode 440 distal to sensor tip 404. As such, exposed surfaces of working electrode 410, working electrode 420, counter electrode 430, and reference electrode 440 are spaced apart from one another along longitudinal axis B of analyte sensor 400.

Referring still to FIG. 6A, creatinine-responsive active areas 414*a* and glucose-responsive active areas 414*b* are disposed upon the exposed surfaces of working electrodes 410 and 420, respectively, thereby allowing contact with a fluid to take place for sensing of creatinine and/or glucose to take place. Although active areas 414*a* and 414*b* have been depicted as three discrete spots in FIG. 6A, it is to be appreciated that fewer or greater than three spots may be present in alternative sensor configurations. Moreover, the positioning of creatinine-responsive active area 414*a* and glucose-responsive active area 414*b* may be reversed from that depicted in FIG. 6A.

In FIG. 6A, sensor 400 is partially coated with membrane 450 upon working electrodes 410 and 420 and active areas 414*a* and 414*b* disposed thereon. FIG. 6B shows an alternative sensor configuration in which the substantial entirety of sensor 401 is overcoated with membrane 450. Membrane 450 may be the same or vary compositionally at active areas 414*a* and 414*b*.

It is to be further appreciated that the positioning of the various electrodes in FIGS. 6A and 6B may differ from that expressly depicted. For example, the positions of counter electrode 430 and reference electrode 440 may be reversed from the depicted configurations in FIGS. 6A and 6B. Similarly, the positions of working electrodes 410 and 420 are not limited to those that are expressly depicted in FIGS. 6A and 6B. FIG. 6C shows an alternative sensor configuration to that shown in FIG. 6B, in which sensor 405 contains counter electrode 430 and reference electrode 440 that are located more proximal to sensor tip 404 and working electrodes 410 and 420 that are located more distal to sensor tip 404. Sensor configurations in which working electrodes 410 and 420 are located more distal to sensor tip 404 may be advantageous by providing a larger surface area for deposition of active areas 414*a* and 414*b* (five discrete sensing spots illustratively shown in FIG. 6C), thereby facilitating an increased signal strength in some cases.

Although FIGS. 6A-6C have depicted sensor configurations that are each supported upon central substrate 402, it is to be appreciated that alternative sensor configurations may be electrode-supported instead and lack central substrate 402. In particular, the innermost concentric electrode may be utilized to support the other electrodes and dielectric layers. FIG. 6D shows an alternative sensor configuration to that depicted in FIG. 6C, in which sensor 406 does not contain central substrate 402 and counter electrode 430 is the innermost concentric electrode and is employed for disposing the reference electrode 440, working electrodes 410 and 420, and dielectric layers 432, 442, 412, and 422 sequentially thereon. In view of the disclosure herein, it is again to be appreciated that other electrode and dielectric layer configurations may be employed in sensor configurations lacking central substrate 402. As such, the sensor configuration depicted in FIG. 6D should be considered illustrative in nature and non-limiting.

As mentioned above, an oxygen scavenger may be located in proximity to the creatinine-responsive active area in order to promote oxidation of the reduced form of sarcosine oxidase with an electron transfer agent instead of with oxygen. An oxidase enzyme, particularly glucose oxidase, may be used for this purpose in the various sensor configurations disclosed herein. When only a creatinine-responsive active area is present, glucose oxidase that is non-functional for glucose detection may be located in proximity to the creatinine-responsive active area. When both a creatinine-responsive active area and a glucose-responsive active area are present, the glucose oxidase in the glucose-responsive active area may effectively promote oxygen scavenging, optionally in combination with glucose oxidase that is non-functional for glucose detection.

Figure 7A:
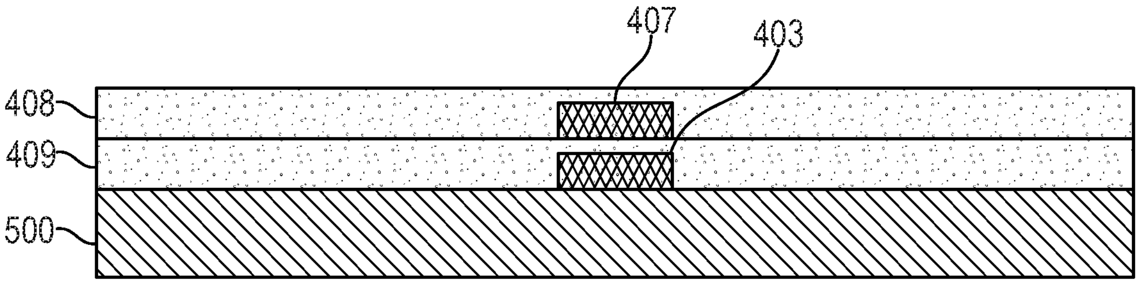
FIGS. 7A and 7B show diagrams of creatinine-responsive active areas having a membrane and an oxygen scavenger disposed thereon.
Figure 7B:
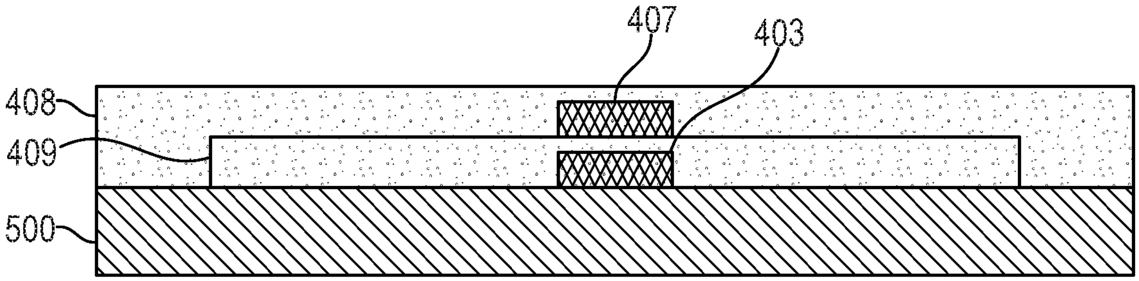

An illustrative disposition for glucose oxidase that is non-functional for glucose detection with respect to a creatinine-responsive active area is shown in FIGS. 7A and 7B. In particular, FIGS. 7A and 7B show diagrams illustrating the disposition of glucose oxidase 407 upon membrane 409 overcoating creatinine-responsive active area 403 positioned upon working electrode 500. Membrane 409 electrically isolates glucose oxidase 407 from working electrode 500, such that electrons generated when oxidizing glucose to limit oxygen exposure are not conveyed to working electrode 500. Membrane 408 subsequently overcoats glucose oxidase 407 to provide a mass transport limiting function thereto. Membranes 408 and 409 may be compositionally the same in various embodiments of the present disclosure. Although FIG. 7A has shown glucose oxidase 407 disposed directly over creatinine-responsive active area 403, it is to be appreciated that creatinine-responsive active area 403 and glucose oxidase 407 may be laterally spaced apart from one another, again provided that glucose oxidase 407 is precluded from transferring electrons to working electrode 500 when oxidizing glucose. Further alternately, glucose oxidase 407 may be additionally located upon an opposite face of the sensor in still other sensor configurations. As shown in FIG. 7B, membrane 409 need not necessarily extend the same lateral distance as does membrane 408 upon working electrode 500.

In the sensor configurations disclosed herein, the creatinine-responsive active area and the glucose-responsive active area, if present, may comprise one or more discrete spots (e.g., one to about ten spots, or even more discrete spots), which may range in size from about 0.01 $mm^2$ to about 1 $mm^2$, although larger or smaller individual spots within the active areas are also contemplated herein. The total active area may be selected to provide a desired sensitivity for each analyte.

In some or other embodiments, analyte sensors of the present disclosure may comprise a sensor tail that is configured for insertion into a tissue. Suitable tissues are not considered to be particularly limited and are addressed in more detail above. Considerations for deploying a sensor tail at a particular position within a given tissue are addressed above.

Accordingly, analyte sensors disclosed herein may comprise a sensor tail comprising at least a first working electrode, a creatinine-responsive active area disposed upon a surface of the first working electrode and comprising a first electron transfer agent, a first polymer, and an enzyme system comprising multiple enzymes that are capable of acting in concert to facilitate detection of creatinine, a first membrane that is permeable to creatinine and overcoats the creatinine-responsive active area, and an oxygen scavenger located upon the sensor tail in proximity to the creatinine-responsive active area. The enzyme system comprises creatinine amidohydrolase, creatine amidinohydrolase, and sarcosine oxidase. The oxygen scavenger may be separated from the creatinine-responsive active area by the first membrane according to particular embodiments of the present disclosure. An oxidase enzyme, such as glucose oxidase, may constitute at least a portion of the oxygen scavenger in some embodiments.

The oxidase enzyme, such as glucose oxidase, may be covalently bonded to a second polymer when disposed in proximity to the creatinine-responsive active area. Suitable polymers for covalently bonding the glucose oxidase are not particularly limited and may be a polyvinylpyridine in particular embodiments of the present disclosure. The covalently bound polymer may aid in immobilizing the glucose oxidase in a desired position with respect to the creatinine-responsive active area.

The creatinine amidohydrolase, the creatine amidinohydrolase, and the sarcosine oxidase may be covalently bonded to the first polymer in the creatinine-responsive active area in any embodiment of the present disclosure. Suitable polymers for covalently bonding these enzymes are not considered to be particularly limited and may be a polyvinylpyridine in particular embodiments of the present disclosure. The first polymer in the creatinine-responsive active area and the second polymer covalently bonded to the glucose oxidase may be the same polymer.

The creatinine-responsive active area and the glucose-responsive active area, if present, may each contain an electron transfer agent in any of the illustrative sensor configurations disclosed herein. When a creatinine-responsive active area and a glucose-responsive active area are both present, the electron transfer agents may be the same or different depending upon the particular sensor configuration employed. Suitable electron transfer agents may facilitate conveyance of electrons to the working electrode after an enzymatic oxidation or reduction reaction takes place, thereby generating a current that is indicative of the presence of a particular analyte and proportional to the quantity of analyte present. For example, when the creatinine-responsive active area and the glucose-responsive active area are disposed upon the same working electrode, the electron transfer agent within each active area may be different (e.g., chemically different such that the electron transfer agents exhibit different oxidation-reduction potentials). When multiple working electrodes are present, the electron transfer agent within each active area may be the same or different, since each working electrode may be interrogated separately when obtaining a signal. The electron-transfer agent may be covalently bonded to a polymer in any of the active areas disclosed herein.

According to various embodiments of the present disclosure, suitable electron transfer agents may include electroreducible and electrooxidizable ions, complexes or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples of suitable electron transfer agents include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable ligands for the metal complexes may also include, for example, bidentate or higher denticity ligands such as, for example, bipyridine, biimidazole, phenanthroline, or pyridyl (imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

Active areas suitable for detecting creatinine and/or glucose may also comprise a polymer to which the electron transfer agents are covalently bonded. Any of the electron transfer agents disclosed herein may comprise suitable functionality to promote covalent bonding to the polymer within the active areas. Suitable examples of polymer-bound electron transfer agents may include those described in U.S. Pat. Nos. 8,444,834, 8,268,143 and 6,605,201, the disclosures of which are incorporated herein by reference in their entirety. Suitable polymers for inclusion in the active areas may include, but are not limited to, polyvinylpyridines (e.g., poly(4-vinylpyridine)), polyvinylimidazoles (e.g., poly(1-vinylimidazole)), or any copolymer thereof. Illustrative copolymers that may be suitable for inclusion in the active areas include those containing monomer units such as styrene, acrylamide, methacrylamide, or acrylonitrile, for example. The polymer within each active area may be the same or different.

In particular embodiments of the present disclosure, the mass transport limiting membrane overcoating the creatinine-responsive active area may comprise at least a cross-linked polyvinylpyridine homopolymer or copolymer, including polyvinylpyridine-co-styrene polymers. A mass transport limiting membrane having a similar composition may overcoat an oxygen scavenger, such as glucose oxidase, as well. The composition of the mass transport limiting membrane may be the same or different where the mass transport limiting membrane overcoats each active area. Suitable techniques for depositing a mass transport limiting membrane upon the active area(s) may include, for example, spray coating, painting, inkjet printing, stenciling, roller coating, dip coating, the like, and any combination thereof.

The manner of covalent bonding between the electron transfer agent and the polymer in each active area is not considered to be particularly limited. Covalent bonding of the electron transfer agent to the polymer may take place by polymerizing a monomer unit bearing a covalently bonded electron transfer agent, or the electron transfer agent may be reacted with the polymer separately after the polymer has already been synthesized. According to some embodiments, a bifunctional spacer may covalently bond the electron transfer agent to the polymer within the active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, one or more of the enzymes within the active areas may be covalently bonded to the polymer. When an enzyme system comprising multiple enzymes is present in a given active area, all of the multiple enzymes may be covalently bonded to the polymer in some embodiments, and in other embodiments, only a portion of the multiple enzymes may be covalently bonded to the polymer. For example, one or more enzymes comprising an enzyme system may be covalently bonded to the polymer and at least one enzyme may be non-covalently associated with the polymer, such that the non-covalently bonded enzyme is physically entrained within the polymer. According to more specific embodiments, covalent bonding of the enzyme(s) to the polymer in a given active area may take place via a crosslinker introduced with a suitable crosslinking agent. Suitable crosslinking agents for reaction with free amino groups in the enzyme (e.g., with the free side chain amine in lysine) may include crosslinking agents such as, for example, polyethylene glycol diglycidyl ether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking of the enzyme to the polymer is generally intermolecular, but can be intramolecular in some embodiments. In particular embodiments, all of the enzymes herein may be covalently bonded to a polymer.

The electron transfer agent and/or the enzyme(s) may be associated with the polymer in the active area through means other than covalent bonding as well. In some embodiments, the electron transfer agent and/or the enzyme(s) may be ionically or coordinatively associated with the polymer. For example, a charged polymer may be ionically associated with an oppositely charged electron transfer agent or enzyme(s). In still other embodiments, the electron transfer agent and/or the enzyme(s) may be physically entrained within the polymer without being bonded thereto. Physically entrained electron transfer agents and/or enzyme(s) may still suitably interact with a fluid to promote analyte detection without being substantially leached from the active areas.

Creatinine-responsive analyte sensors may further incorporate a glucose-responsive active area for sensing both creatinine and glucose, in some embodiments of the present disclosure. When both a creatinine-responsive active area and a glucose-responsive active area are present, the creatinine-responsive active area and the glucose-responsive active area may be present upon the same working electrode or different working electrodes as discussed above in reference to FIGS. 4A-6C. Considerations for incorporating a glucose-responsive active area in either location are discussed in further detail below. In any sensor configuration herein that includes both a creatinine-responsive active area and a glucose-responsive active area, glucose oxidase that is non-functional for glucose detection may be disposed upon a membrane overcoating the creatinine-responsive active area or in another location that is unable to convey electrons to the working electrode associated with the creatinine-responsive active area.

When a creatinine-responsive active area and a glucose-responsive active area are arranged upon a single working electrode, one of the active areas may be configured such that it can be interrogated separately to facilitate detection of each analyte, as described hereinafter. In particular, the creatinine-responsive active area and the glucose-responsive active area may comprise different electron transfer agents to allow one of the active areas to produce a signal independently of the other. Either of the creatinine-responsive active area or the glucose-responsive active area may configured to produce a signal independently of the other active area.

In embodiments wherein the creatinine-responsive active area and the glucose-responsive active area are arranged upon a single working electrode, the oxidation-reduction potential associated with the glucose-responsive active area may be separated from the oxidation-reduction potential of the creatinine-responsive active area by at least about 100 mV, or by at least about 150 mV, or by at least about 200 mV. The upper limit of the separation between the oxidation-reduction potentials is dictated by the working electrochemical window in vivo. By having the oxidation-reduction potentials of the two active areas sufficiently separated in magnitude from one another, an electrochemical reaction make take place within one of the two active areas (i.e., within the glucose-responsive active area or the creatinine-responsive active area) without substantially inducing an electrochemical reaction within the other active area. Thus, a signal from one of the glucose-responsive active area or the creatinine-responsive active area may be independently produced at or above its corresponding oxidation-reduction potential (the lower oxidation-reduction potential) but below the oxidation-reduction potential of the other of the glucose-responsive active area and the creatinine-responsive active area (the higher oxidation-reduction potential). At or above the oxidation-reduction potential (the higher oxidation-reduction potential) of the other active area that was not previously interrogated, in contrast, electrochemical reactions may occur within both the glucose-responsive active area and the creatinine-responsive active area. As such, the resulting signal at or above the higher oxidation-reduction potential may include a signal contribution from both the glucose-responsive active area and the creatinine-responsive active area, and the observed signal is a composite signal. The signal contribution from one active area (either the glucose-responsive active area or the creatinine-responsive active area) at or above its oxidation-reduction potential may then be determined by subtracting from the composite signal the signal obtained solely from either the glucose-responsive active area or the creatinine-responsive active area at or above its corresponding oxidation-reduction potential.

In more specific embodiments, the glucose-responsive active area and the creatinine-responsive active area may contain different electron transfer agents when the active areas are located upon the same working electrode, so as to afford oxidation-reduction potentials that are sufficiently separated in magnitude from one another. More specifically, the glucose-responsive active area may comprise a first electron transfer agent and the creatinine-responsive active area may comprise a second electron transfer agent, with the first and second electron transfer agents being different. The metal center and/or the ligands present in a given electron transfer agent may be varied to provide sufficient separation of the oxidation-reduction potentials within the two active areas, according to various embodiments of the present disclosure.

Ideally, a glucose-responsive active area and a creatinine-responsive active area located upon a single working electrode may be configured to attain a steady state current rapidly upon operating the analyte sensor at a given potential. Rapid attainment of a steady state current may be promoted by choosing an electron transfer agent for each active area that changes its oxidation state quickly upon being exposed to a potential at or above its oxidation-reduction potential. Making the active areas as thin as possible may also facilitate rapid attainment of a steady state current. For example, suitable thicknesses for the glucose-responsive active area and creatinine-responsive active area may range from about 0.1 microns to about 10 microns. In some or other embodiments, combining a conductive material such as, for example, carbon nanotubes, graphene, or metal nanoparticles within one or more of the active areas may promote rapid attainment of a steady state current. Suitable amounts of conductive particles may range from about 0.1% to about 50% by weight of the active area, or from about 1% to about 50% by weight, or from about 0.1% to about 10% by weight, or from about 1% to about 10% by weight. Stabilizers may also be employed to promote response stability.

It is also to be appreciated that the sensitivity (output current) of the analyte sensors toward each analyte may be varied by changing the coverage (area or size) of the active areas, the areal ratio of the active areas with respect to one another, the identity, thickness and/or composition of a mass transport limiting membrane overcoating the active areas. Variation of these parameters may be conducted readily by one having ordinary skill in the art once granted the benefit of the disclosure herein.

Other embodiments of analyte sensors disclosed herein may feature the creatinine-responsive active area and the glucose-responsive active area upon the surface of different working electrodes. Such analyte sensors may further comprise a second working electrode, a glucose-responsive active area disposed upon a surface of the second working electrode, and a second membrane that is permeable to glucose overcoating the glucose-responsive active area. The glucose-responsive active area may comprise a second electron transfer agent, a third polymer, and glucose oxidase that is covalently bonded to the third polymer. The third polymer may be the same as or different than the first and/or second polymer associated with the creatinine-responsive active area or the glucose oxidase that is non-functional for detecting glucose, respectively. When the creatinine-responsive active area and the glucose-responsive active area are disposed upon separate working electrodes, the electron transfer agent associated with each active area may be the same or different.

Accordingly, certain analyte sensors of the present disclosure that are capable of detecting both creatinine and glucose may comprise: a sensor tail comprising a first working electrode and a second working electrode; a creatinine-responsive active area disposed upon a surface of the first working electrode, the creatinine-responsive active area comprising a first electron transfer agent, a first polymer, and an enzyme system comprising multiple enzymes that are capable of acting in concert to facilitate detection of creatinine, the enzyme system comprising: creatinine amidohydrolase, creatine amidinohydrolase, and sarcosine oxidase; a first membrane that is permeable to creatinine and overcoats the creatinine-responsive active area; glucose oxidase covalently bonded to a second polymer and disposed upon the first membrane; a glucose-responsive active area disposed upon a surface of the second working electrode, the glucose-responsive active area comprising a second electron transfer agent, a third polymer and glucose oxidase that is covalently bonded to the third polymer; and a second membrane that is permeable to glucose and overcoats the glucose-responsive active area. Such analyte sensors may further comprise a third membrane overcoating the glucose oxidase that is disposed upon the first membrane. The first membrane, the second membrane and the third membrane, if present, may be compositionally the same in particular embodiments.

Detection methods for assaying creatinine may comprise: exposing an analyte sensor to a fluid comprising at least creatinine, wherein the analyte sensor comprises a sensor tail comprising at least a first working electrode, a creatinine-responsive active area disposed upon a surface of the first working electrode, a first membrane that is permeable to creatinine and overcoats the creatinine-responsive active area, and an oxygen scavenger located upon the sensor tail in proximity to the creatinine-responsive active area. The creatinine-responsive active area comprises a first electron transfer agent, a first polymer, an enzyme system comprising multiple enzymes that are capable of acting in concert to facilitate detection of creatinine. The enzyme system comprises creatinine amidohydrolase, creatine amidinohydrolase, and sarcosine oxidase, all of which may be covalently bonded to the first polymer in particular embodiments. The methods may further comprise applying a potential to the first working electrode, obtaining a first signal at or above an oxidation-reduction potential of the creatinine-responsive active area that is proportional to a concentration of creatinine in the fluid, and correlating the first signal to the concentration of creatinine in the fluid. The fluid may be a biological fluid in particular embodiments of the present disclosure. Glucose may be present in the fluid in combination with creatinine in still more particular embodiments.

In some embodiments, the first signal may be correlated to a corresponding concentration of creatinine by consulting a lookup table or calibration curve. A lookup table for creatinine may be populated by assaying multiple samples having known creatinine concentrations and recording the sensor response at each concentration. Similarly, a calibration curve for creatinine may be determined by plotting the analyte sensor response as a function of the creatinine concentration and determining a suitable calibration function over the calibration range (e.g., by regression, particularly linear regression).

A processor may determine which sensor response value in a lookup table is closest to that measured for a sample having an unknown analyte concentration and then report the analyte concentration accordingly. In some or other embodiments, if the sensor response value for a sample having an unknown analyte concentration is between the recorded values in the lookup table, the processor may interpolate between two lookup table values to estimate the analyte concentration. Interpolation may assume a linear concentration variation between the two values reported in the lookup table. Interpolation may be employed when the sensor response differs a sufficient amount from a given value in the lookup table, such as variation of about 10% or greater.

Likewise, according to some or other various embodiments, a processor may input the sensor response value for a sample having an unknown analyte concentration into a corresponding calibration function. The processor may then report the analyte concentration accordingly.

The sensor tail may further comprise a second working electrode having a glucose-responsive active area disposed thereon, and in which the glucose-responsive active area may comprise a second electron transfer agent, a third polymer, and glucose oxidase that is covalently bonded to the third polymer. As such, the methods may further comprise: applying a potential to the second working electrode, obtaining a second signal at or above an oxidation-reduction potential of the glucose-responsive active area that is proportional to a concentration of glucose in the fluid, and correlating the second signal to the concentration of glucose in the fluid.

Detection methods for assaying creatinine and/or glucose using an analyte sensor featuring a creatinine-responsive active area and a glucose-responsive active area upon a single working electrode may comprise: exposing an analyte sensor to a fluid comprising at least one of creatinine and glucose. The analyte sensor may comprise a sensor tail comprising at least a working electrode, particularly a single working electrode, and at least a creatinine-responsive active area and a glucose-responsive active area disposed upon a surface of the working electrode and that are spaced apart from each other. A membrane may overcoat the creatinine-responsive active area, and glucose oxidase covalently bound to a polymer may be disposed upon the membrane, in addition to glucose oxidase in the glucose-responsive active area. The creatinine-responsive active area comprises an enzyme system comprising two or more enzymes that are capable of acting in concert to facilitate detection of creatinine, a first polymer covalently bonded to the enzymes, and a first electron transfer agent covalently bonded to the first polymer. The glucose-responsive active area comprises glucose oxidase, a third polymer covalently bonded to the glucose oxidase, and a second electron transfer agent covalently bonded to the third polymer. When the glucose-responsive active area and the creatinine-responsive active area are located upon a single working electrode, the first and second electron transfer agents differ compositionally from one another, as discussed in more detail herein. Each active area has an oxidation-reduction potential, and the oxidation-reduction potential of the creatinine-responsive active area is sufficiently separated from the oxidation-reduction potential of the glucose-responsive active area to allow production of a signal from one of the active areas. The methods additionally comprise: obtaining a first signal at or above a lower of the oxidation-reduction potentials but below a higher of the oxidation-reduction potentials, such that the first signal is proportional to a concentration of one of glucose or creatinine in the fluid; obtaining a second signal at or above a higher of the oxidation-reduction potentials, such that the second signal is a composite signal comprising a signal contribution from the glucose-responsive active area and a signal contribution from the creatinine-responsive active area; and subtracting the first signal from the second signal to obtain a difference signal, the difference signal being proportional to a concentration of one of glucose and creatinine.

In more specific embodiments, the oxidation-reduction potential associated with the creatinine-responsive active area may be separated from the oxidation-reduction potential of the glucose-responsive active area by at least about 100 mV, or by at least about 150 mV, or by at least about 200 mV in order to provide sufficient separation for independent production of a signal from the first active area. The differing oxidation-reduction potentials may result from incorporating different electron transfer agents in the active areas.

Detection methods for assaying creatinine and/or glucose employing an analyte sensor featuring a creatinine-responsive active area and a glucose-responsive active area upon separate working electrodes may comprise: exposing an analyte sensor to a fluid comprising at least one of glucose and creatinine. The analyte sensor comprises a sensor tail comprising at least a first working electrode and second working electrode, a creatinine-responsive active area disposed upon a surface of the first working electrode, a glucose-responsive active area disposed upon a surface of the second working electrode, and a first membrane overcoating the creatinine-responsive active area, and a second membrane overcoating the glucose-responsive active area. The glucose-responsive active area comprises a glucose-responsive enzyme, such as glucose oxidase, and the creatinine-responsive active area comprises an enzyme system comprising at least two enzymes that are capable of acting in concert to facilitate detection of creatinine.

The methods may additionally comprise applying a potential to the first working electrode and a potential to the second working electrode, obtaining a first signal at or above an oxidation-reduction potential of the creatinine-responsive active area, in which the first signal is proportional to a concentration of creatinine in the fluid, obtaining a second signal at or above an oxidation-reduction potential of the glucose-responsive active area, in which the second signal is proportional to a concentration of glucose in the fluid, and correlating the first signal to the concentration of creatinine in the fluid and the second signal to the concentration of glucose in the fluid.

According to more specific embodiments, the first signal and the second signal maybe measured at different times. Thus, in such embodiments, a potential may be alternately applied to the first working electrode and the second working electrode. In other specific embodiments, the first signal and the second signal may be measured simultaneously via a first channel and a second channel, in which case a potential may be applied to both electrodes at the same time. In either case, the signal associated with each active area may then be correlated to the concentration of creatinine and glucose using a lookup table or a calibration function in a similar manner to that discussed above.

Embodiments disclosed herein include:

A. Analyte sensors responsive to creatinine. The analyte sensors comprise: a sensor tail comprising at least a first working electrode; a creatinine-responsive active area disposed upon a surface of the first working electrode, the creatinine-responsive active area comprising a first electron transfer agent, a first polymer, and an enzyme system comprising multiple enzymes that are capable of acting in concert to facilitate detection of creatinine, the enzyme system comprising: creatinine amidohydrolase, creatine amidinohydrolase, and sarcosine oxidase; a first membrane that is permeable to creatinine and overcoats the creatinine-responsive active area; and an oxygen scavenger located upon the sensor tail in proximity to the creatinine-responsive active area.

B. Analyte sensors responsive to creatinine and glucose. The analyte sensors comprise: a sensor tail comprising a first working electrode and a second working electrode; a creatinine-responsive active area disposed upon a surface of the first working electrode, the creatinine-responsive active area comprising a first electron transfer agent, a first polymer, and an enzyme system comprising multiple enzymes that are capable of acting in concert to facilitate detection of creatinine, the enzyme system comprising: creatinine amidohydrolase, creatine amidinohydrolase, and sarcosine oxidase; a first membrane that is permeable to creatinine and overcoats the creatinine-responsive active area; glucose oxidase covalently bonded to a second polymer and disposed upon the first membrane; a glucose-responsive active area disposed upon a surface of the second working electrode, the glucose-responsive active area comprising a second electron transfer agent, a third polymer, and glucose oxidase that is covalently bonded to the third polymer; and a second membrane that is permeable to glucose and overcoats the glucose-responsive active area.

C. Methods for assaying creatinine using an analyte sensor. The methods comprise: exposing an analyte sensor to a fluid comprising at least creatinine; wherein the analyte sensor comprises a sensor tail comprising at least a first working electrode, a creatinine-responsive active area disposed upon a surface of the first working electrode, a first membrane that is permeable to creatinine and overcoats the creatinine-responsive active area, and oxygen scavenger located upon the sensor tail in proximity to the creatinine-responsive active area; wherein the creatinine-responsive active area comprises a first electron transfer agent, a first polymer, and an enzyme system comprising multiple enzymes that are capable of acting in concert to facilitate detection of creatinine, the enzyme system comprising: creatinine amidohydrolase, creatine amidinohydrolase, and sarcosine oxidase; applying a potential to the first working electrode; obtaining a first signal at or above an oxidation-reduction potential of the creatinine-responsive active area, the first signal being proportional to a concentration of creatinine in the fluid; and correlating the first signal to the concentration of creatinine in the fluid. Each of embodiments A-D may have one or more of the following additional elements in any combination:

Element 1: wherein the oxygen scavenger is separated from the creatinine-responsive active area by the first membrane.

Element 2: wherein the oxygen scavenger comprises an oxidase enzyme.

Element 3: wherein the oxygen scavenger comprises glucose oxidase.

Element 4: wherein the glucose oxidase is covalently bonded to a second polymer.

Element 5: wherein the oxygen scavenger is disposed upon the first membrane, optionally wherein the oxygen scavenger comprises an oxidase enzyme, optionally wherein the oxygen scavenger comprises glucose oxidase, optionally wherein the glucose oxidase is covalently bonded to a second polymer.

Element 6: wherein the creatinine amidohydrolase, the creatine amidinohydrolase, and the sarcosine oxidase are each covalently bonded to the first polymer.

Element 7: wherein the analyte sensor further comprises a second working electrode; a glucose-responsive active area disposed upon a surface of the second working electrode, the glucose-responsive active area comprising a second electron transfer agent, a third polymer, and glucose oxidase that is covalently bonded to the third polymer; and a second membrane that is permeable to glucose and overcoats the glucose-responsive active area.

Element 8: wherein the analyte sensor further comprises glucose oxidase covalently bonded to a second polymer and disposed upon the first membrane.

Element 9: wherein the first membrane and the second membrane are compositionally the same.

Element 10: wherein the glucose oxidase disposed upon the first membrane is overcoated by a third membrane that is also permeable to creatinine.

Element 11: wherein the first membrane, the second membrane and the third membrane are compositionally the same.

Element 12: wherein the oxygen scavenger is disposed upon the first membrane.

Element 13: wherein the oxygen scavenger comprises glucose oxidase that is covalently bonded to a second polymer.

Element 14: wherein the sensor tail further comprises a second working electrode having a glucose-responsive active area disposed upon a surface of the second working electrode, the glucose-responsive active area comprising a second electron transfer agent, a third polymer, and glucose oxidase that is covalently bonded to the third polymer, the method further comprising: applying a potential to the second working electrode; obtaining a second signal at or above an oxidation-reduction potential of the glucose-responsive active area, the second signal being proportional to a concentration of glucose in the fluid; and correlating the second signal to the concentration of glucose in the fluid.

Element 15: wherein the first signal and the second signal are obtained at different times.

Element 16: wherein the first signal and the second signal are obtained simultaneously via a first channel and a second channel.

By way of non-limiting example, exemplary combinations applicable to A include: 1 and 2; 1 and 3; 1, 3 and 4; 1 and 5; 1, 5 and 6; 1 and 7; 1, 3 and 7; 1, 3, 4 and 7; 1, 5 and 7; 1 and 5-7; 1 and 8; 1, 7 and 8; 1, 3, 4 and 7; 1, 5 and 7; 1 and 5-7; 1, 6 and 7; 1, 3, 4, 6 and 7; 1, 3, 4 and 6-8; 1, 3, 4, 6, 7 and 9; 1 and 5-10; 1 and 5-11; 1 and 5-12; 2 and 3; 2-4; 2 and 6; 2 and 7; 3 and 6; 3, 6 and 7; 3 and 7; 3 and 8; 3, 7 and 8; 3, 8 and 9; 3, 7 and 8; 3 and 7-9; 3 and 8-10; 3 and 8-11; 3 and 8-12; 3, 4 and 7; 3, 4, 8 and 9; 3, 4 and 7-10; 3, 4 and 7-11; 4 and 5; 5 and 6; 5-7; 5 and 7; 7 and 9; 7, 9 and 10; 7 and 9-11; 7 and 8; and 8 and 9. Exemplary combinations applicable to B include 10 and 11; 9 and 10; 6 and 10; and 6 and 11. Exemplary combinations applicable to C include 1 and 3; 1 and 6; 1, 3 and 6; 1 and 9; 1, 3 and 9; 1, 3 and 10; 1, 3, 10 and 11; 6 and 12; 6 and 13; 6 and 14; 6 and 15; 6 and 16; 12 and 13; 12 and 14; 12 and 15; 12 and 16; 13 and 14; 13 and 15; 13 and 16; 14 and 15; and 14 and 16.

To facilitate a better understanding of the disclosure herein, the following examples of various representative embodiments are given. In no way should the following examples be read to limit, or to define, the scope of the invention.

EXAMPLES

A poly(vinylpyridine)-bound transition metal complex having the structure shown in Formula 1 was prepared. Further details concerning this transition metal complex and electron transfer therewith is provided in commonly owned U.S. Pat. No. 6,605,200, which was incorporated by reference above. The subscripts for each monomer represent illustrative atomic ratios and are not indicative of any particular monomer ordering.

Formula 1

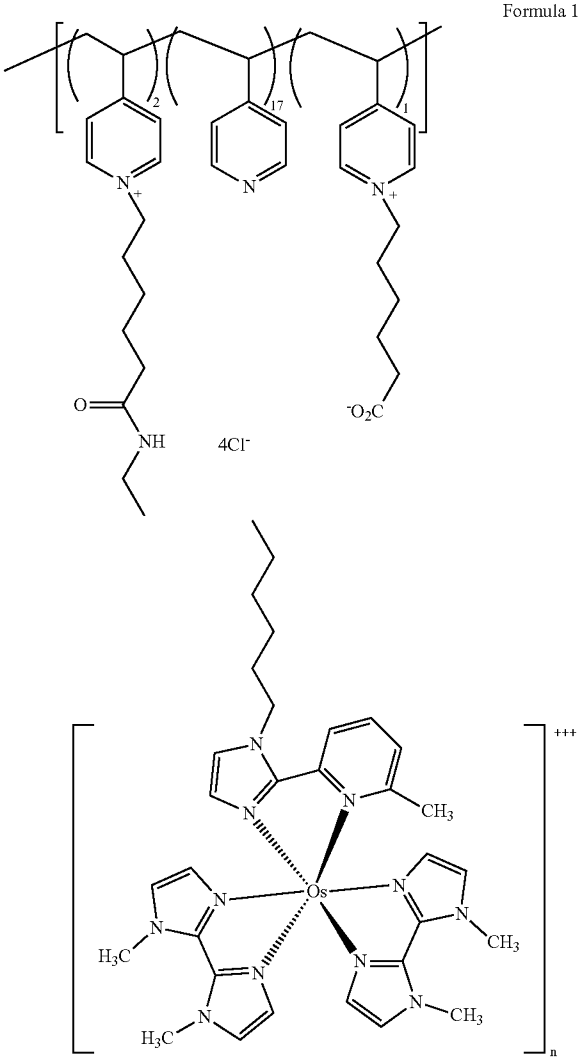

A buffered spotting formulation (10 mM MES buffer) specified in Table 1 below was deposited on a carbon working electrode to form a creatinine-responsive active area. Deposition was performed with 15 nL of the spotting formulation to form a creatinine-responsive active area as a single spot having an area of 0.12 $mm^2$. Following deposition, the creatinine-responsive active area was cured overnight at 25° C. Thereafter, a membrane was dip coated onto the creatinine-responsive active area using a coating solution formulated with 4 mL of 35 mg/mL polyvinylpyridine-co-styrene, 0.1 mL of 100 mg/mL PEGDGE400, and 3.3 μL PDMS in 80:20 ethanol/10 mM HEPES buffer (pH=8). No curing was performed at this stage.

TABLE 1

| Component | Concentration (mg/mL) |
|---|---|
| CNH | 20 |
| CRH | 40 |
| SOX | 5 |
| Formula 1 Polymer | 8.5 |
| PEGDGE400 | 6.5 |

After coating the membrane upon the creatinine-responsive active area, a buffered spotting formulation containing glucose oxidase, as specified in Table 2, was deposited upon the membrane. Specifically, 15 nL of the spotting formulation was deposited upon the membrane in an area of 0.05 $mm^2$ and curing was then conducted at 25° C. overnight. Thereafter, dip coating was performed using the same coating solution specified above to form a membrane upon the deposited glucose oxidase.

TABLE 2

| Component | Concentration (mg/mL) |
|---|---|
| GOX | 32.8 |
| PVI (pH = 5.8) | 27.2 |
| PEGDGE400 | 10 |

A control electrode was prepared as above, except omitting the glucose oxidase deposition upon the creatinine-responsive active area.

Figure 8:
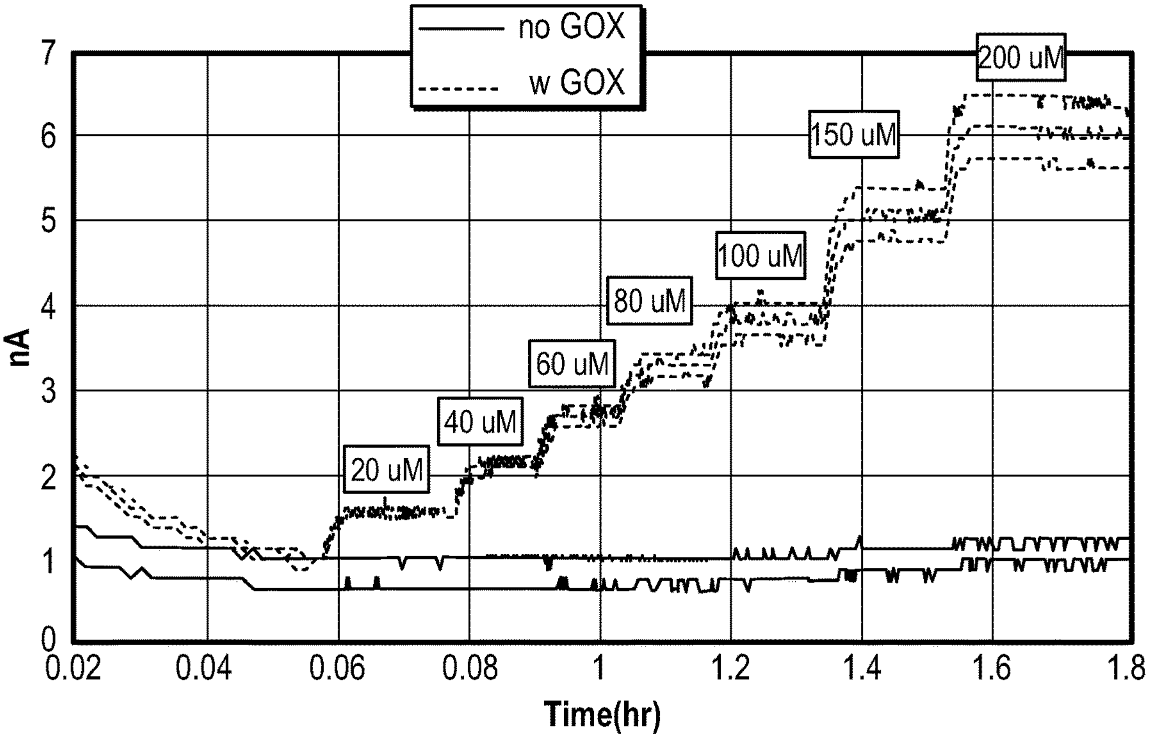
FIG. 8 shows an illustrative plot of the current response for three replicates of a sensor containing a creatinine-responsive active area overcoated with glucose oxidase when exposed to varying creatinine concentrations.
Figure 9:
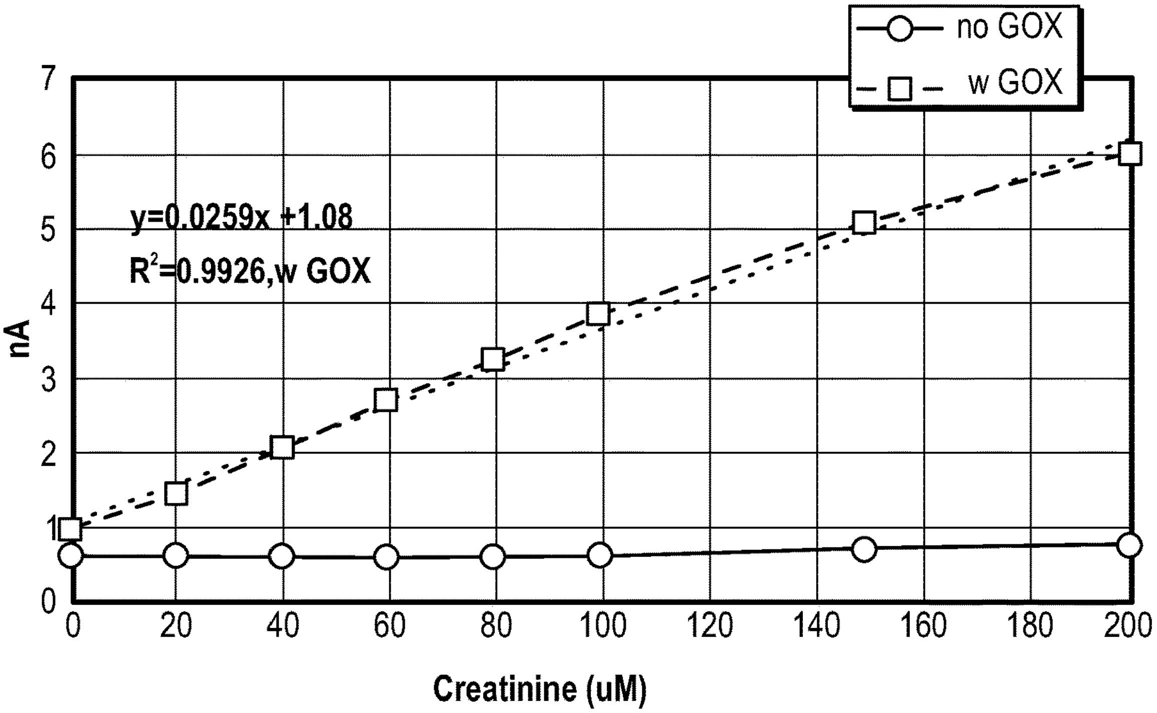
FIG. 9 shows an illustrative plot of the current response for a single sensor containing a creatinine-responsive active area overcoated with glucose oxidase when exposed to various creatinine concentrations.

Creatinine analyses were conducted by immersing the electrode in a 5 mM glucose solution also containing various amounts of creatinine (20 μM, 40 μM, 60 μM, 80 μM, 100 μM, 130 μM, and 200 μM) and measuring the current response. The control electrode lacking glucose oxidase upon the creatinine-responsive active area was also tested under the same conditions. FIG. 8 shows an illustrative plot of the current response for three replicates of an analyte sensor containing a creatinine-responsive active area overcoated with glucose oxidase when exposed to varying creatinine concentrations at 33° C. As shown, the current response increased over the course of several minutes following exposure to a new creatinine concentration before stabilizing thereafter. In contrast, two control sensors lacking glucose oxidase overcoating upon the creatinine-responsive active area were unresponsive to creatinine at any concentration. FIG. 9 shows an illustrative plot of the current response for a single analyte sensor containing a creatinine-responsive active area overcoated with glucose oxidase when exposed to varying creatinine concentrations (20 μM, 40 μM, 60 μM, 80 μM, 100 μM, 130 μM, and 200 μM). As shown, the sensor response was essentially linear over the tested concentration range. A control sensor lacking glucose oxidase overcoating again showed essentially no response to creatinine, likely due to oxygen interference with the enzyme system.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. An analyte sensor comprising:

at least a first working electrode;

a creatinine-responsive active area disposed on a distal end of the first working electrode, the creatinine-responsive active area comprising a first electron transfer agent, a first polymer, and an enzyme system comprising multiple enzymes that are capable of acting in concert to facilitate detection of creatinine, the enzyme system comprising:

creatinine amidohydrolase, creatine amidinohydrolase, and sarcosine oxidase;

a dielectric layer covering the first working electrode other than the distal end of the first working electrode;

a first membrane that is permeable to creatinine and overcoats the creatinine-responsive active area, the first membrane comprising polyvinylpyridine-co-styrene; and an area for oxygen scavenging disposed upon the first membrane and isolated from the first working electrode, the area for oxygen scavenging comprising glucose oxidase as an oxygen scavenger, wherein the sensor is configured to be partially inserted into a tissue such that a distal portion of the sensor is in contact with an interstitial fluid to detect creatinine in vivo.

2. The analyte sensor of claim 1, wherein the area for oxygen scavenging further comprises a second polymer and the glucose oxidase is covalently bonded to the second polymer.

3. The analyte sensor of claim 1, wherein the creatinine amidohydrolase, the creatine amidinohydrolase, and the sarcosine oxidase are each covalently bonded to the first polymer.

4. The analyte sensor of claim 1, further comprising:

a second working electrode;

a glucose-responsive active area disposed upon a surface of the second working electrode, the glucose-responsive active area comprising a second electron transfer agent, a third polymer, and glucose oxidase that is covalently bonded to the third polymer; and a second membrane that is permeable to glucose and overcoats the glucose-responsive active area.

5. The analyte sensor of claim 4, wherein the first membrane and the second membrane are compositionally the same.

6. An analyte sensor comprising:

a first working electrode and a second working electrode;

a creatinine-responsive active area disposed on a distal end of the first working electrode, the creatinine-responsive active area comprising a first electron transfer agent, a first polymer, and an enzyme system comprising multiple enzymes that are capable of acting in concert to facilitate detection of creatinine, the enzyme system comprising:

creatinine amidohydrolase, creatine amidinohydrolase, and sarcosine oxidase;

a dielectric layer covering the first working electrode other than the distal end of the first working electrode;

a first membrane that is permeable to creatinine and overcoats the creatinine-responsive active area, the first membrane comprising polyvinylpyridine-co-styrene;

an area for oxygen scavenging disposed upon the first membrane and isolated from the first working electrode, the area for oxygen scavenging comprising a second polymer and glucose oxidase as an oxygen scavenger, the glucose oxidase covalently bonded to the second polymer;

a glucose-responsive active area disposed upon a surface of the second working electrode, the glucose-responsive active area comprising a second electron transfer agent, a third polymer, and glucose oxidase that is covalently bonded to the third polymer; and a second membrane that is permeable to glucose and overcoats the glucose-responsive active area, wherein the sensor is configured to be partially inserted into a tissue such that a distal portion of the sensor is in contact with an interstitial fluid to detect glucose and creatinine in vivo.

7. The analyte sensor of claim 6, wherein the area for oxygen scavenging is overcoated by a third membrane that is also permeable to creatinine.

8. The analyte sensor of claim 7, wherein the first membrane, the second membrane and the third membrane are compositionally the same.

9. The analyte sensor of claim 6, wherein the first membrane and the second membrane are compositionally the same.

10. The analyte sensor of claim 6, wherein the creatinine amidohydrolase, the creatine amidinohydrolase, and the sarcosine oxidase are each covalently bonded to the first polymer.

11. A method comprising:

exposing the analyte sensor of claim 1 to a fluid comprising at least creatinine;

applying a potential to the first working electrode;

obtaining a first signal at or above an oxidation-reduction potential of the creatinine-responsive active area, the first signal being proportional to a concentration of creatinine in the fluid; and correlating the first signal to the concentration of creatinine in the fluid.

12. The method of claim 11, wherein the creatinine amidohydrolase, the creatine amidinohydrolase, and the sarcosine oxidase are each covalently bonded to the first polymer.

13. The method of claim 11, wherein the area for oxygen scavenging further comprises a second polymer and the glucose oxidase is covalently bonded to the second polymer.

14. The method of claim 12, wherein the sensor further comprises a second working electrode having a glucose-responsive active area disposed upon a surface of the second working electrode, the glucose-responsive active area comprising a second electron transfer agent, a third polymer, and glucose oxidase that is covalently bonded to the third polymer, the method further comprising:

applying a potential to the second working electrode;

obtaining a second signal at or above an oxidation-reduction potential of the glucose-responsive active area, the second signal being proportional to a concentration of glucose in the fluid; and correlating the second signal to the concentration of glucose in the fluid.

15. The method of claim 14, wherein the first signal and the second signal are obtained at different times.

16. The method of claim 14, wherein the first signal and the second signal are obtained simultaneously via a first channel and a second channel.

* * * * *